(12) United States Patent
DiMauro et al.

(10) Patent No.: US 9,839,460 B2
(45) Date of Patent: Dec. 12, 2017

(54) REMOTELY-ACTIVATED VERTEBROPLASTY INJECTION DEVICE

(75) Inventors: Thomas M. DiMauro, Southboro, MA (US); John Crombie, East Hanover, NJ (US); Richard Pellegrino, Mendon, MA (US); Martin A. Reynolds, Mansfield, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 2010 days.

(21) Appl. No.: 12/388,563

(22) Filed: Feb. 19, 2009

(65) Prior Publication Data

US 2009/0270872 A1 Oct. 29, 2009

Related U.S. Application Data

(63) Continuation of application No. 10/405,113, filed on Mar. 31, 2003.

(51) Int. Cl.
| | | |
|---|---|---|
| *A61B 17/58* | (2006.01) | |
| *A61M 1/00* | (2006.01) | |
| *A61B 17/88* | (2006.01) | |
| *A61F 2/46* | (2006.01) | |
| *A61F 2/30* | (2006.01) | |
| *A61F 2/48* | (2006.01) | |

(52) U.S. Cl.
CPC ........ *A61B 17/8822* (2013.01); *A61F 2/4601* (2013.01); *A61F 2002/3008* (2013.01); *A61F 2002/30523* (2013.01); *A61F 2002/48* (2013.01); *A61F 2220/0025* (2013.01); *A61F 2250/0098* (2013.01)

(58) Field of Classification Search
USPC .............................................. 606/93–94, 92
See application file for complete search history.

(56) References Cited

U.S. PATENT DOCUMENTS

| 229,932 A | 7/1880 | Witsil |
|---|---|---|
| 370,335 A | 9/1887 | Hunter |
| (Continued) | | |

FOREIGN PATENT DOCUMENTS

| AU | 724544 | 11/1996 |
|---|---|---|
| AU | 9865136 | 9/1998 |
| (Continued) | | |

OTHER PUBLICATIONS

Andersen, M. et al., "Vertebroplastik, ny behandling af osteoporotiske columnafrakturer?", Ugeskr Laefer 166/6:463-66 (Feb. 2, 2004).

(Continued)

*Primary Examiner* — Christian Sevilla
(74) *Attorney, Agent, or Firm* — Nutter McClennen & Fish LLP

(57) ABSTRACT

A remotely-activated injection device for use in vertebroplasty is provided to inject a flourescent probe material into a patient. The injection device includes a pump defining an injection chamber having an exit opening; an actuator; and a cable having a first end coupled to the actuator, and a second end remotely engaging the pump. The actuator remotely controls the pump by responsive movement of the cable to thereby cause injection of a flourescent probe material from the injection chamber of the pump through the exit opening to the patient.

8 Claims, 10 Drawing Sheets

(56) References Cited

U.S. PATENT DOCUMENTS

| | | |
|---|---|---|
| 817,973 A | 4/1906 | Hausman |
| 833,044 A | 10/1906 | Goodhugh |
| 843,587 A | 2/1907 | DePew |
| 1,175,530 A | 3/1916 | Kirchoff |
| 1,612,281 A | 12/1926 | Goetz |
| 1,612,996 A | 1/1927 | Waagbo |
| 1,733,516 A | 10/1929 | Jamison |
| 1,894,274 A | 1/1933 | Jacques |
| 1,929,247 A | 10/1933 | Hein |
| 408,668 A | 4/1934 | Norman et al. |
| 2,123,712 A | 7/1938 | Clark |
| 2,283,915 A | 5/1942 | Cole |
| 2,394,488 A | 2/1946 | Rotter et al. |
| 2,425,867 A | 8/1947 | Davis |
| 2,435,647 A | 2/1948 | Engseth |
| 2,497,762 A | 2/1950 | Davis |
| 2,521,569 A | 9/1950 | Davis |
| 2,567,960 A | 9/1951 | Meyers et al. |
| 2,745,575 A | 5/1956 | Spencer |
| 2,773,500 A | 12/1956 | Young |
| 2,808,239 A | 10/1957 | Alfred |
| 2,874,877 A | 2/1959 | Spencer |
| 2,918,841 A | 12/1959 | Poupitch |
| 2,928,574 A | 3/1960 | Wagner |
| 2,970,773 A | 2/1961 | Horace et al. |
| 3,058,413 A | 11/1962 | Cavalieri |
| 3,063,449 A | 11/1962 | Schultz |
| 3,075,746 A | 1/1963 | Yablonski et al. |
| 3,108,593 A | 10/1963 | Glassman |
| 3,151,847 A | 10/1964 | Broomall |
| 3,198,194 A | 8/1965 | Wilburn |
| 3,216,616 A | 11/1965 | Blankenship, Jr. |
| 3,224,744 A | 12/1965 | Broomall |
| 3,225,760 A | 12/1965 | Di Cosola |
| 3,254,494 A | 6/1966 | Chartouni |
| 3,362,793 A | 1/1968 | Massoubre |
| 3,381,566 A | 5/1968 | Passer |
| 3,426,364 A | 2/1969 | Lumb |
| 3,515,873 A | 6/1970 | Higgins |
| 3,559,956 A | 2/1971 | Gray |
| 3,568,885 A | 3/1971 | Spencer |
| 3,572,556 A | 3/1971 | Pogacar |
| 3,605,745 A | 9/1971 | Hodosh |
| 3,615,240 A | 10/1971 | Sanz |
| 3,674,011 A | 7/1972 | Michel et al. |
| 3,701,350 A | 10/1972 | Guenther |
| 3,750,667 A | 8/1973 | Pshenichny et al. |
| 3,789,727 A | 2/1974 | Moran |
| 3,796,303 A | 3/1974 | Abbel-Coche |
| 3,798,982 A | 3/1974 | Lundquist |
| 3,846,846 A | 11/1974 | Fischer |
| 3,850,158 A | 11/1974 | Elias et al. |
| 3,867,728 A | 2/1975 | Stubstad et al. |
| 3,873,008 A | 3/1975 | Jahn |
| 3,875,595 A | 4/1975 | Froning |
| 3,896,504 A | 7/1975 | Fischer |
| 3,901,408 A | 8/1975 | Boden et al. |
| 3,921,858 A | 11/1975 | Bemm |
| 3,931,914 A | 1/1976 | Hosaka et al. |
| 3,942,407 A | 3/1976 | Mortensen |
| 3,976,060 A | 8/1976 | Hildebrandt et al. |
| 3,993,250 A | 11/1976 | Shure |
| 4,011,602 A | 3/1977 | Rybicki et al. |
| 4,062,274 A | 12/1977 | Knab |
| 4,077,494 A | 3/1978 | Spaude et al. |
| 4,079,917 A | 3/1978 | Popeil |
| 4,090,640 A | 5/1978 | Smith et al. |
| 4,093,576 A | 6/1978 | Dewijn |
| 4,105,145 A | 8/1978 | Capra |
| 4,115,346 A | 9/1978 | Gross et al. |
| 4,146,334 A | 3/1979 | Farrell |
| 4,168,787 A | 9/1979 | Stamper |
| 4,170,990 A | 10/1979 | Baumgart et al. |
| 4,180,070 A | 12/1979 | Genese |
| 4,185,072 A | 1/1980 | Puderbaugh et al. |
| 4,189,065 A | 2/1980 | Herold |
| 4,198,383 A | 4/1980 | Konsetov et al. |
| 4,198,975 A | 4/1980 | Haller |
| 4,204,531 A | 5/1980 | Aginsky |
| 4,239,113 A | 12/1980 | Gross et al. |
| 4,250,887 A | 2/1981 | Dardik et al. |
| 4,257,540 A | 3/1981 | Wegmann et al. |
| 4,268,639 A | 5/1981 | Seidel et al. |
| 4,274,163 A | 6/1981 | Malcom et al. |
| 4,276,878 A | 7/1981 | Storz |
| 4,277,184 A | 7/1981 | Solomon |
| 4,298,144 A | 11/1981 | Pressl |
| 4,309,777 A | 1/1982 | Patil |
| 4,312,343 A | 1/1982 | LeVeen et al. |
| 4,313,434 A | 2/1982 | Segal |
| 4,326,567 A | 4/1982 | Mistarz |
| 4,338,925 A | 7/1982 | Miller |
| 4,341,691 A | 7/1982 | Anuta |
| 4,346,708 A | 8/1982 | LeVeen et al. |
| 4,349,921 A | 9/1982 | Kuntz |
| 4,359,049 A | 11/1982 | Redl et al. |
| 4,373,217 A | 2/1983 | Draenert |
| 4,380,398 A | 4/1983 | Burgess |
| 4,400,170 A | 8/1983 | McNaughton et al. |
| 4,403,989 A | 9/1983 | Christensen et al. |
| 4,404,327 A | 9/1983 | Crugnola et al. |
| 4,405,249 A | 9/1983 | Scales |
| 4,409,966 A | 10/1983 | Lambrecht et al. |
| 4,453,539 A | 6/1984 | Raftopoulos et al. |
| 4,474,572 A | 10/1984 | McNaughton et al. |
| 4,475,856 A | 10/1984 | Toomingas |
| 4,476,866 A | 10/1984 | Chin |
| 4,487,602 A | 12/1984 | Christensen et al. |
| 4,494,535 A | 1/1985 | Haig |
| 4,500,658 A | 2/1985 | Fox |
| 4,503,169 A | 3/1985 | Randklev |
| 4,522,200 A | 6/1985 | Stednitz |
| D279,499 S | 7/1985 | Case |
| 4,543,966 A | 10/1985 | Islam et al. |
| 4,546,767 A | 10/1985 | Smith |
| 4,554,914 A | 11/1985 | Kapp et al. |
| 4,558,693 A | 12/1985 | Lash et al. |
| 4,562,598 A | 1/1986 | Kranz |
| 4,576,152 A | 3/1986 | Muller et al. |
| 4,588,583 A | 5/1986 | Pietsch et al. |
| 4,593,685 A | 6/1986 | McKay et al. |
| 4,595,006 A | 6/1986 | Burke et al. |
| 4,600,118 A | 7/1986 | Martin |
| 4,605,011 A | 8/1986 | Naslund |
| 4,632,101 A | 12/1986 | Freedland |
| 4,636,217 A | 1/1987 | Ogilvie et al. |
| 4,642,099 A | 2/1987 | Phillips et al. |
| 4,650,469 A | 3/1987 | Berg et al. |
| 4,651,904 A | 3/1987 | Schuckmann |
| 4,653,487 A | 3/1987 | Maale |
| 4,653,489 A | 3/1987 | Tronzo et al. |
| 4,664,298 A | 5/1987 | Shew |
| 4,664,655 A | 5/1987 | Orentreich et al. |
| 4,668,220 A | 5/1987 | Hawrylenko |
| 4,668,295 A | 5/1987 | Bajpai |
| 4,670,008 A | 6/1987 | Von Albertini |
| 4,671,263 A | 6/1987 | Draenert |
| 4,676,655 A | 6/1987 | Handler |
| 4,676,781 A | 6/1987 | Phillips et al. |
| 4,686,973 A | 8/1987 | Frisch |
| 4,697,584 A | 10/1987 | Haynes |
| 4,697,929 A | 10/1987 | Muller |
| 4,704,035 A | 11/1987 | Kowalczyk |
| 4,710,179 A | 12/1987 | Haber et al. |
| 4,714,721 A | 12/1987 | Franek et al. |
| 4,717,383 A | 1/1988 | Phillips et al. |
| 4,718,910 A | 1/1988 | Draenert |
| 4,722,948 A | 2/1988 | Sanderson |
| 4,735,616 A | 4/1988 | Eibl et al. |
| 4,737,151 A | 4/1988 | Clement et al. |
| 4,747,832 A | 5/1988 | Buffet |
| 4,758,096 A | 7/1988 | Gunnarsson |
| 4,758,234 A | 7/1988 | Orentreich et al. |
| 4,759,769 A | 7/1988 | Hedman et al. |

(56) References Cited

U.S. PATENT DOCUMENTS

| | | |
|---|---|---|
| 4,762,515 A | 8/1988 | Grimm |
| 4,767,033 A | 8/1988 | Gemperle |
| 4,772,287 A | 9/1988 | Ray et al. |
| 4,782,118 A | 11/1988 | Fontanille et al. |
| 4,786,184 A | 11/1988 | Berezkina et al. |
| 4,791,150 A | 12/1988 | Braden et al. |
| 4,792,577 A | 12/1988 | Chen et al. |
| 2,067,458 A | 2/1989 | Nichols |
| 4,804,023 A | 2/1989 | Frearson |
| 4,813,870 A | 3/1989 | Pitzen |
| 4,815,454 A | 3/1989 | Dozier |
| 4,815,632 A | 3/1989 | Ball et al. |
| 4,826,053 A | 5/1989 | Keller |
| 4,830,227 A | 5/1989 | Ball et al. |
| 4,837,279 A | 6/1989 | Arroyo |
| 4,854,312 A | 8/1989 | Raftopoulos et al. |
| 4,854,482 A | 8/1989 | Bergner |
| 4,854,716 A | 8/1989 | Ziemann et al. |
| 4,863,072 A | 9/1989 | Perler |
| 4,869,906 A | 9/1989 | Dingeldein et al. |
| 4,872,936 A | 10/1989 | Engelbrecht |
| 4,892,231 A | 1/1990 | Ball |
| 4,892,550 A | 1/1990 | Huebsch |
| 4,902,649 A | 2/1990 | Kimura et al. |
| 4,904,260 A | 2/1990 | Ray et al. |
| 4,908,017 A | 3/1990 | Howson et al. |
| 4,910,259 A | 3/1990 | Kindt-Larsen et al. |
| 4,927,866 A | 5/1990 | Purrmann et al. |
| 4,932,969 A | 6/1990 | Frey et al. |
| 4,935,029 A | 6/1990 | Matsutani et al. |
| 4,944,065 A | 7/1990 | Svanberg et al. |
| 4,944,726 A | 7/1990 | Hilal et al. |
| 4,946,077 A | 8/1990 | Olsen |
| 4,946,285 A | 8/1990 | Vennemeyer |
| 4,946,901 A | 8/1990 | Lechner et al. |
| 4,961,647 A | 10/1990 | Coutts et al. |
| 4,966,601 A | 10/1990 | Draenert |
| 4,968,303 A | 11/1990 | Clarke et al. |
| 4,969,888 A | 11/1990 | Scholten et al. |
| 4,973,168 A | 11/1990 | Chan |
| 4,973,301 A | 11/1990 | Nissenkorn |
| 4,973,334 A | 11/1990 | Ziemann |
| 4,978,336 A | 12/1990 | Capozzi et al. |
| 4,983,164 A | 1/1991 | Hook et al. |
| 4,994,065 A | 2/1991 | Gibbs et al. |
| 4,995,868 A | 2/1991 | Brazier |
| 5,004,501 A | 4/1991 | Faccioli et al. |
| 5,006,112 A | 4/1991 | Metzner |
| 5,012,066 A | 4/1991 | Matsutani et al. |
| 5,015,233 A | 5/1991 | McGough et al. |
| 5,018,919 A | 5/1991 | Stephan |
| 5,022,563 A | 6/1991 | Marchitto et al. |
| 5,024,232 A | 6/1991 | Smid et al. |
| 5,028,141 A | 7/1991 | Stiegelmann |
| 5,037,473 A | 8/1991 | Antonucci et al. |
| 5,049,157 A | 9/1991 | Mittelmeier et al. |
| 5,051,482 A | 9/1991 | Tepic |
| 5,059,193 A | 10/1991 | Kuslich |
| 5,059,199 A | 10/1991 | Okada et al. |
| 5,061,128 A | 10/1991 | Jahr et al. |
| 5,071,040 A | 12/1991 | Laptewicz, Jr. |
| 5,074,871 A | 12/1991 | Groshong |
| 5,078,919 A | 1/1992 | Ashley et al. |
| 5,092,888 A | 3/1992 | Iwamoto et al. |
| 5,102,413 A | 4/1992 | Poddar |
| 5,108,403 A | 4/1992 | Stern |
| 5,108,404 A | 4/1992 | Scholten et al. |
| 5,112,333 A | 5/1992 | Fixel |
| 5,114,240 A | 5/1992 | Kindt-Larsen et al. |
| 5,116,335 A | 5/1992 | Hannon |
| 5,122,400 A | 6/1992 | Stewart |
| 5,123,926 A | 6/1992 | Pisharodi |
| 5,125,971 A | 6/1992 | Nonami et al. |
| 5,131,382 A | 7/1992 | Meyer |
| 5,141,496 A | 8/1992 | Dalto et al. |
| 5,145,250 A | 9/1992 | Planck et al. |
| 5,147,903 A | 9/1992 | Podszun et al. |
| 5,171,248 A | 12/1992 | Ellis |
| 5,171,278 A | 12/1992 | Pisharodi |
| 5,181,918 A | 1/1993 | Brandhorst et al. |
| 5,188,259 A | 2/1993 | Petit |
| 5,190,191 A | 3/1993 | Reyman |
| 5,192,327 A | 3/1993 | Brantigan |
| 5,193,907 A | 3/1993 | Faccioli |
| 5,209,753 A | 5/1993 | Biedermann et al. |
| 5,217,147 A | 6/1993 | Kaufman |
| 5,219,897 A | 6/1993 | Murray |
| 5,236,445 A | 8/1993 | Hayhurst et al. |
| 5,242,983 A | 9/1993 | Kennedy et al. |
| 5,252,301 A | 10/1993 | Nilson et al. |
| 5,254,092 A | 10/1993 | Polyak |
| 5,258,420 A | 11/1993 | Posey-Dowty et al. |
| 5,264,215 A | 11/1993 | Nakabayashi et al. |
| 5,268,001 A | 12/1993 | Nicholson et al. |
| 5,269,762 A | 12/1993 | Armbruster et al. |
| 5,275,214 A | 1/1994 | Rehberger |
| 5,276,070 A | 1/1994 | Arroyo |
| 5,277,339 A | 1/1994 | Shew et al. |
| 5,279,555 A | 1/1994 | Lifshey |
| 5,290,260 A | 3/1994 | Stines |
| 5,295,980 A | 3/1994 | Ersek |
| 5,302,020 A | 4/1994 | Kruse |
| 5,303,718 A | 4/1994 | Krajicek |
| 5,304,147 A | 4/1994 | Johnson et al. |
| 5,318,532 A | 6/1994 | Frassica |
| 5,328,262 A | 7/1994 | Lidgren et al. |
| 5,328,362 A | 7/1994 | Watson et al. |
| 5,331,972 A | 7/1994 | Wadhwani et al. |
| 5,333,951 A | 8/1994 | Wakoh |
| 5,334,184 A | 8/1994 | Bimman |
| 5,334,626 A | 8/1994 | Lin |
| 5,336,699 A | 8/1994 | Cooke et al. |
| 5,336,700 A | 8/1994 | Murray |
| 5,344,232 A | 9/1994 | Nelson et al. |
| 5,348,391 A | 9/1994 | Murray |
| 5,348,548 A | 9/1994 | Meyer et al. |
| 5,350,372 A | 9/1994 | Ikeda et al. |
| 5,354,287 A | 10/1994 | Wacks |
| 5,356,382 A | 10/1994 | Picha et al. |
| 5,368,046 A | 11/1994 | Scarfone et al. |
| 5,368,386 A | 11/1994 | Murray |
| 5,370,221 A | 12/1994 | Magnusson et al. |
| 5,372,583 A | 12/1994 | Roberts |
| 5,374,427 A | 12/1994 | Stille et al. |
| 5,376,123 A | 12/1994 | Klaue et al. |
| 5,380,772 A | 1/1995 | Hasegawa et al. |
| 5,385,081 A | 1/1995 | Sneddon |
| 5,385,566 A | 1/1995 | Ullmaerk |
| 5,387,191 A | 2/1995 | Hemstreet et al. |
| 5,390,683 A | 2/1995 | Pisharodi |
| 5,395,167 A | 3/1995 | Murray |
| 5,395,326 A | 3/1995 | Haber et al. |
| 5,398,483 A | 3/1995 | Smith et al. |
| 5,401,806 A | 3/1995 | Braden et al. |
| 5,407,266 A | 4/1995 | Dotsch et al. |
| 5,411,180 A | 5/1995 | Dumelle |
| 5,415,474 A | 5/1995 | Nelson et al. |
| 5,423,824 A | 6/1995 | Akerfeldt et al. |
| 5,423,850 A | 6/1995 | Berger |
| 5,431,654 A | 7/1995 | Nic |
| 5,435,645 A | 7/1995 | Faccioli |
| 5,441,502 A | 8/1995 | Bartlett |
| 5,443,182 A | 8/1995 | Tanaka et al. |
| 5,445,639 A | 8/1995 | Kuslich et al. |
| 5,450,924 A | 9/1995 | Tseng |
| 5,454,365 A | 10/1995 | Bonutti |
| 5,456,267 A | 10/1995 | Stark |
| 5,468,245 A | 11/1995 | Vargas, III |
| 5,480,400 A | 1/1996 | Berger |
| 5,480,403 A | 1/1996 | Lee |
| 5,482,187 A | 1/1996 | Poulsen et al. |
| 5,492,247 A | 2/1996 | Shu et al. |
| 5,494,349 A | 2/1996 | Seddon |
| 5,501,374 A | 3/1996 | Laufer et al. |

(56) References Cited

U.S. PATENT DOCUMENTS

| | | |
|---|---|---|
| 5,501,520 A | 3/1996 | Lidgren et al. |
| 5,501,695 A | 3/1996 | Anspach, Jr. et al. |
| 5,512,610 A | 4/1996 | Lin |
| 5,514,135 A | 5/1996 | Earle |
| 5,514,137 A | 5/1996 | Coutts |
| 5,518,498 A | 5/1996 | Lindenberg et al. |
| 5,520,690 A | 5/1996 | Errico et al. |
| 5,522,816 A | 6/1996 | Dinello et al. |
| 5,522,899 A | 6/1996 | Michelson |
| 5,526,853 A | 6/1996 | McPhee et al. |
| 5,531,519 A | 7/1996 | Earle |
| 5,531,683 A | 7/1996 | Kriesel et al. |
| 5,534,028 A | 7/1996 | Bao et al. |
| 5,536,262 A | 7/1996 | Velasquez |
| 5,545,460 A | 8/1996 | Tanaka et al. |
| 5,548,001 A | 8/1996 | Podszun et al. |
| 5,549,380 A | 8/1996 | Lidgren et al. |
| 5,549,381 A | 8/1996 | Hays et al. |
| 5,549,679 A | 8/1996 | Kuslich |
| 5,551,778 A | 9/1996 | Hauke et al. |
| 5,554,101 A | 9/1996 | Matula et al. |
| 5,556,201 A | 9/1996 | Veltrop et al. |
| 5,558,136 A | 9/1996 | Orrico |
| 5,558,639 A | 9/1996 | Gangemi et al. |
| 5,571,189 A | 11/1996 | Kuslich et al. |
| 5,573,265 A | 11/1996 | Pradel |
| 5,578,035 A | 11/1996 | Lin |
| 5,586,821 A | 12/1996 | Bonitati et al. |
| 5,588,745 A | 12/1996 | Tanaka et al. |
| 5,591,197 A | 1/1997 | Orth et al. |
| 5,601,557 A | 2/1997 | Hayhurst |
| 5,603,701 A | 2/1997 | Fischer |
| 5,609,637 A | 3/1997 | Biedermann et al. |
| 5,624,184 A | 4/1997 | Chan |
| 5,630,806 A | 5/1997 | Inagaki et al. |
| 5,634,880 A | 6/1997 | Feldman et al. |
| 5,637,097 A | 6/1997 | Yoon |
| 5,638,997 A | 6/1997 | Hawkins et al. |
| 5,641,010 A | 6/1997 | Maier |
| 5,645,598 A | 7/1997 | Brosnahan, III |
| 5,647,856 A | 7/1997 | Eykmann |
| 5,653,686 A | 8/1997 | Coulter et al. |
| 5,658,310 A | 8/1997 | Berger |
| 5,660,186 A | 8/1997 | Bachir |
| 5,665,067 A | 9/1997 | Linder et al. |
| 5,681,317 A | 10/1997 | Caldarise |
| 5,683,451 A | 11/1997 | Lenker et al. |
| 5,685,826 A | 11/1997 | Bonutti |
| 5,690,606 A | 11/1997 | Slotman |
| 5,693,100 A | 12/1997 | Pisharodi |
| 5,697,977 A | 12/1997 | Pisharodi |
| 5,698,611 A | 12/1997 | Okada et al. |
| 5,702,448 A | 12/1997 | Buechel et al. |
| 5,704,895 A | 1/1998 | Scott et al. |
| 5,707,390 A | 1/1998 | Bonutti |
| 5,718,707 A | 2/1998 | Mikhail |
| 5,720,753 A | 2/1998 | Sander et al. |
| 5,725,341 A | 3/1998 | Hofmeister |
| 5,725,529 A | 3/1998 | Nicholson et al. |
| 5,747,553 A | 5/1998 | Guzauskas |
| 5,752,935 A | 5/1998 | Robinson et al. |
| 5,752,969 A | 5/1998 | Cunci |
| 5,752,974 A | 5/1998 | Rhee |
| 5,755,732 A | 5/1998 | Green et al. |
| 5,759,186 A | 6/1998 | Bachmann et al. |
| 5,763,092 A | 6/1998 | Lee et al. |
| 5,779,356 A | 7/1998 | Chan |
| 5,782,713 A | 7/1998 | Yang |
| 5,782,747 A | 7/1998 | Zimmon |
| 5,782,830 A | 7/1998 | Farris |
| 5,782,838 A | 7/1998 | Beyar et al. |
| 5,785,647 A | 7/1998 | Tompkins et al. |
| 5,785,682 A | 7/1998 | Grabenkort |
| 5,792,044 A | 8/1998 | Foley |
| 5,795,922 A | 8/1998 | Demian et al. |
| 5,797,678 A | 8/1998 | Murray |
| 5,800,169 A | 9/1998 | Muhlbauer |
| 5,800,409 A | 9/1998 | Bruce |
| 5,800,549 A | 9/1998 | Bao et al. |
| 5,800,550 A | 9/1998 | Sertich |
| 5,820,321 A | 10/1998 | Gruber |
| 5,824,087 A | 10/1998 | Aspden et al. |
| 5,826,713 A | 10/1998 | Sunago et al. |
| 5,826,753 A | 10/1998 | Fehlig et al. |
| 5,827,217 A | 10/1998 | Silver et al. |
| 5,827,289 A | 10/1998 | Reiley et al. |
| 5,829,875 A | 11/1998 | Hagel et al. |
| 5,830,194 A | 11/1998 | Anwar et al. |
| 5,836,306 A | 11/1998 | Duane et al. |
| 5,839,621 A | 11/1998 | Tada |
| 5,842,785 A | 12/1998 | Brown et al. |
| 5,865,802 A | 2/1999 | Yoon et al. |
| 5,876,116 A | 3/1999 | Barker et al. |
| 5,876,457 A | 3/1999 | Picha et al. |
| 5,882,340 A | 3/1999 | Yoon et al. |
| 5,884,818 A | 3/1999 | Campbell |
| 5,893,488 A | 4/1999 | Hoag et al. |
| 5,893,850 A | 4/1999 | Cachia |
| 5,902,839 A | 5/1999 | Lautenschlager et al. |
| 5,911,721 A | 6/1999 | Nicholson et al. |
| 5,918,702 A | 7/1999 | Cheng et al. |
| 5,918,770 A | 7/1999 | Camm et al. |
| 5,925,051 A | 7/1999 | Mikhail |
| 5,928,239 A | 7/1999 | Mirza |
| 5,931,347 A | 8/1999 | Haubrich |
| 5,941,851 A | 8/1999 | Coffey et al. |
| 5,954,671 A | 9/1999 | O'Neill |
| 5,954,728 A | 9/1999 | Heller et al. |
| 5,961,211 A | 10/1999 | Barker et al. |
| 5,968,008 A | 10/1999 | Grams |
| 5,968,044 A | 10/1999 | Nicholson et al. |
| 5,968,999 A | 10/1999 | Ramp et al. |
| 5,972,015 A | 10/1999 | Scribner et al. |
| 5,980,527 A | 11/1999 | Cohen et al. |
| 5,993,535 A | 11/1999 | Sawamura et al. |
| 5,997,544 A | 12/1999 | Nies et al. |
| 6,004,325 A | 12/1999 | Vargas, III |
| 6,007,496 A | 12/1999 | Brannon |
| 6,017,349 A | 1/2000 | Heller et al. |
| 6,019,765 A | 2/2000 | Thornhill et al. |
| 6,019,776 A | 2/2000 | Preissman et al. |
| 6,019,789 A | 2/2000 | Dinh et al. |
| 6,020,396 A | 2/2000 | Jacobs |
| 6,022,339 A | 2/2000 | Fowles et al. |
| 6,033,105 A | 3/2000 | Barker et al. |
| 6,033,411 A | 3/2000 | Preissman |
| 6,039,761 A | 3/2000 | Li et al. |
| 6,040,408 A | 3/2000 | Koole |
| 6,041,977 A | 3/2000 | Lisi |
| 6,042,262 A | 3/2000 | Hajianpour |
| 6,045,555 A | 4/2000 | Smith et al. |
| 6,048,346 A | 4/2000 | Reiley |
| 6,049,026 A | 4/2000 | Muschler |
| 6,075,067 A | 6/2000 | Lidgren |
| 6,080,579 A | 6/2000 | Hanley, Jr. |
| 6,080,801 A | 6/2000 | Draenert et al. |
| 6,080,811 A | 6/2000 | Schehlmann et al. |
| 6,083,229 A | 7/2000 | Constantz et al. |
| 6,086,594 A | 7/2000 | Brown |
| 6,103,779 A | 8/2000 | Guzauskas |
| 6,116,773 A | 9/2000 | Murray |
| 6,120,174 A | 9/2000 | Hoag et al. |
| 6,124,373 A | 9/2000 | Peter et al. |
| 6,126,689 A | 10/2000 | Brett |
| 6,127,597 A | 10/2000 | Beyar et al. |
| 6,129,763 A | 10/2000 | Chauvin et al. |
| 6,132,396 A | 10/2000 | Antanavich et al. |
| 6,136,038 A | 10/2000 | Raab |
| 6,139,509 A | 10/2000 | Yuan et al. |
| 6,142,998 A | 11/2000 | Smith et al. |
| 6,146,401 A | 11/2000 | Yoon et al. |
| 6,149,651 A | 11/2000 | Drewry et al. |
| 6,149,655 A | 11/2000 | Constantz et al. |
| 6,149,664 A | 11/2000 | Kurz |

(56) References Cited

U.S. PATENT DOCUMENTS

| | | |
|---|---|---|
| 6,160,033 A | 12/2000 | Nies |
| 6,161,955 A | 12/2000 | Rademaker |
| 6,168,597 B1 | 1/2001 | Biedermann et al. |
| 6,174,935 B1 | 1/2001 | Matsunae et al. |
| 6,176,607 B1 | 1/2001 | Hajianpour |
| 6,183,441 B1 | 2/2001 | Kriesel et al. |
| 6,183,516 B1 | 2/2001 | Burkinshaw et al. |
| 6,187,015 B1 | 2/2001 | Brenneman |
| 6,190,381 B1 | 2/2001 | Olsen et al. |
| 6,206,058 B1 | 3/2001 | Nagel et al. |
| 6,210,031 B1 | 4/2001 | Murray |
| 6,214,012 B1 | 4/2001 | Karpman et al. |
| 6,214,016 B1 | 4/2001 | Williams et al. |
| 6,214,037 B1 | 4/2001 | Mitchell et al. |
| 6,217,566 B1 | 4/2001 | Ju et al. |
| 6,217,581 B1 | 4/2001 | Tolson |
| 6,217,608 B1 | 4/2001 | Penn et al. |
| 6,221,029 B1 | 4/2001 | Mathis et al. |
| 6,224,604 B1 | 5/2001 | Suddaby |
| 6,228,049 B1 | 5/2001 | Schroeder et al. |
| 6,228,068 B1 | 5/2001 | Yoon |
| 6,228,082 B1 | 5/2001 | Baker et al. |
| 6,231,615 B1 | 5/2001 | Preissman |
| 6,235,043 B1 | 5/2001 | Reiley et al. |
| 6,238,399 B1 | 5/2001 | Heller et al. |
| 6,241,734 B1 | 6/2001 | Scribner et al. |
| 6,245,101 B1 | 6/2001 | Drasler et al. |
| 6,248,110 B1 | 6/2001 | Reiley et al. |
| 6,254,268 B1 | 7/2001 | Long |
| 6,261,289 B1 | 7/2001 | Levy |
| 6,264,618 B1 | 7/2001 | Landi et al. |
| 6,264,659 B1 * | 7/2001 | Ross et al. ............... 606/93 |
| 6,264,660 B1 | 7/2001 | Schmidt et al. |
| 6,273,916 B1 | 8/2001 | Murphy |
| 6,281,271 B1 | 8/2001 | Rumphorst et al. |
| 6,309,395 B1 | 10/2001 | Smith et al. |
| 6,309,420 B1 | 10/2001 | Preissman |
| 6,312,149 B1 | 11/2001 | Sojovall et al. |
| 6,325,812 B1 | 12/2001 | Dubrul et al. |
| 6,348,055 B1 | 2/2002 | Preissman |
| 6,348,518 B1 | 2/2002 | Montgomery |
| 6,350,271 B1 | 2/2002 | Kurz et al. |
| 6,361,539 B1 | 3/2002 | Heller et al. |
| 6,364,865 B1 | 4/2002 | Lavi et al. |
| 6,367,962 B1 | 4/2002 | Mizutani et al. |
| 6,375,659 B1 | 4/2002 | Erbe et al. |
| 6,375,682 B1 | 4/2002 | Fleischmann et al. |
| 6,383,188 B2 | 5/2002 | Kuslich et al. |
| 6,383,190 B1 | 5/2002 | Preissman |
| 6,395,007 B1 | 5/2002 | Bhatnagar et al. |
| 6,402,701 B1 | 6/2002 | Kaplan et al. |
| 6,402,758 B1 | 6/2002 | Tolson |
| 6,406,175 B1 | 6/2002 | Marino |
| 6,409,972 B1 | 6/2002 | Chan |
| 6,410,612 B1 | 6/2002 | Hatanaka |
| 6,425,887 B1 | 7/2002 | McGuckin et al. |
| 6,431,743 B1 | 8/2002 | Mizutani et al. |
| 6,433,037 B1 | 8/2002 | Guzauskas |
| 6,436,143 B1 | 8/2002 | Ross et al. |
| 6,439,439 B1 | 8/2002 | Rickard |
| 6,443,334 B1 | 9/2002 | John et al. |
| 6,447,478 B1 | 9/2002 | Maynards |
| 6,450,973 B1 | 9/2002 | Murphy |
| 6,458,117 B1 | 10/2002 | Pollins, Sr. |
| 6,479,565 B1 | 11/2002 | Stanley |
| 6,488,667 B1 | 12/2002 | Murphy |
| 6,494,868 B2 | 12/2002 | Amar |
| 6,500,182 B2 | 12/2002 | Foster |
| 6,502,608 B1 | 1/2003 | Burchett et al. |
| 6,527,144 B2 | 3/2003 | Ritsche et al. |
| 6,550,957 B2 | 4/2003 | Mizutani et al. |
| 6,554,833 B2 | 4/2003 | Levy et al. |
| 6,568,439 B1 | 5/2003 | Se et al. |
| 6,572,256 B2 | 6/2003 | Seaton et al. |
| 6,575,331 B1 | 6/2003 | Peeler et al. |
| 6,575,919 B1 | 6/2003 | Reiley et al. |
| 6,582,439 B1 | 6/2003 | Sproul |
| 6,592,559 B1 | 7/2003 | Pakter et al. |
| 6,595,967 B2 | 7/2003 | Kramer |
| 6,599,293 B2 | 7/2003 | Tague et al. |
| 6,599,520 B2 | 7/2003 | Scarborough et al. |
| 6,613,018 B2 | 9/2003 | Bagga et al. |
| 6,613,054 B2 | 9/2003 | Scribner et al. |
| 6,626,912 B2 | 9/2003 | Speitling |
| 6,641,587 B2 | 11/2003 | Scribner et al. |
| 6,645,213 B2 | 11/2003 | Sand et al. |
| 6,662,969 B2 | 12/2003 | Peeler et al. |
| 6,676,664 B1 | 1/2004 | Al-Assir |
| 6,689,823 B1 | 2/2004 | Bellare et al. |
| 6,702,455 B2 | 3/2004 | Vendrely et al. |
| 6,712,853 B2 | 3/2004 | Kuslich |
| 6,716,216 B1 | 4/2004 | Boucher et al. |
| 6,719,761 B1 | 4/2004 | Reiley et al. |
| 6,720,417 B1 | 4/2004 | Walter |
| 6,730,095 B2 | 5/2004 | Olson, Jr. et al. |
| 6,752,180 B2 | 6/2004 | Delay |
| 6,758,837 B2 | 7/2004 | Peclat et al. |
| 6,759,449 B2 | 7/2004 | Kimura et al. |
| 6,767,973 B2 | 7/2004 | Suau et al. |
| 6,770,079 B2 | 8/2004 | Bhatnagar |
| 6,779,566 B2 | 8/2004 | Engel |
| 6,780,175 B1 | 8/2004 | Sachdeva et al. |
| 6,783,515 B1 | 8/2004 | Miller et al. |
| 6,787,584 B2 | 9/2004 | Jia et al. |
| 6,796,987 B2 | 9/2004 | Tague et al. |
| 6,852,439 B2 | 2/2005 | Frank |
| 6,874,927 B2 | 4/2005 | Foster |
| 6,875,219 B2 | 4/2005 | Arramon et al. |
| 6,887,246 B2 | 5/2005 | Bhatnagar |
| 6,916,308 B2 | 7/2005 | Dixon et al. |
| 6,957,747 B2 | 10/2005 | Peeler et al. |
| 6,974,247 B2 | 12/2005 | Frei et al. |
| 6,974,416 B2 | 12/2005 | Booker et al. |
| 6,979,341 B2 | 12/2005 | Scribner et al. |
| 6,979,352 B2 | 12/2005 | Reynolds |
| 6,994,465 B2 | 2/2006 | Tague et al. |
| 6,997,930 B1 | 2/2006 | Jaggi |
| 7,008,433 B2 | 3/2006 | Voellmicke et al. |
| 7,025,771 B2 | 4/2006 | Kuslich et al. |
| 7,029,163 B2 | 4/2006 | Barker et al. |
| 7,044,954 B2 | 5/2006 | Reiley |
| 7,048,743 B2 | 5/2006 | Miller |
| 7,066,942 B2 | 6/2006 | Treace |
| 7,087,040 B2 | 8/2006 | McGuckin |
| 7,091,258 B2 | 8/2006 | Neubert et al. |
| 7,097,648 B1 | 8/2006 | Globerman et al. |
| 7,112,205 B2 | 9/2006 | Carrison |
| 7,116,121 B1 | 10/2006 | Holcombe et al. |
| 7,252,671 B2 | 8/2007 | Scribner |
| 7,264,622 B2 | 9/2007 | Michelson |
| 7,270,667 B2 | 9/2007 | Faccioli |
| 7,278,778 B2 | 10/2007 | Sand |
| 7,320,540 B2 | 1/2008 | Coffeen |
| 7,326,203 B2 | 2/2008 | Papineau et al. |
| 7,456,024 B2 | 11/2008 | Dahm et al. |
| 7,470,258 B2 | 12/2008 | Barker et al. |
| 7,559,932 B2 | 7/2009 | Truckai et al. |
| 7,572,263 B2 | 8/2009 | Preissman |
| 7,575,577 B2 | 8/2009 | Boyd et al. |
| 7,604,618 B2 | 10/2009 | Dixon et al. |
| 7,666,205 B2 | 2/2010 | Weikel et al. |
| 7,678,116 B2 | 3/2010 | Truckai et al. |
| 7,717,918 B2 | 5/2010 | Truckai et al. |
| 7,722,620 B2 | 5/2010 | Truckai et al. |
| 8,038,682 B2 | 10/2011 | McGill et al. |
| 8,066,713 B2 | 11/2011 | DiMauro et al. |
| 8,070,753 B2 | 12/2011 | Truckai et al. |
| 8,360,629 B2 | 1/2013 | Globerman et al. |
| 8,361,078 B2 | 1/2013 | Beyar et al. |
| 8,415,407 B2 | 4/2013 | Beyar et al. |
| 8,540,722 B2 | 9/2013 | Beyar et al. |
| 8,809,418 B2 | 8/2014 | Beyar et al. |
| 8,950,929 B2 | 2/2015 | Globerman et al. |
| 8,956,368 B2 | 2/2015 | Beyar et al. |

(56) References Cited

U.S. PATENT DOCUMENTS

| | | |
|---|---|---|
| 9,186,194 B2 | 11/2015 | Ferreyro et al. |
| 9,259,696 B2 | 2/2016 | Globerman et al. |
| 9,381,024 B2 | 7/2016 | Globerman et al. |
| 9,504,508 B2 | 11/2016 | Beyar et al. |
| 9,642,932 B2 | 5/2017 | Beyar et al. |
| 2001/0012968 A1 | 8/2001 | Preissman |
| 2001/0024400 A1 | 9/2001 | Van Der Wel |
| 2001/0034527 A1 | 10/2001 | Scribner et al. |
| 2002/0008122 A1 | 1/2002 | Ritsche et al. |
| 2002/0010471 A1 | 1/2002 | Wironen et al. |
| 2002/0010472 A1 | 1/2002 | Kuslich et al. |
| 2002/0013553 A1 | 1/2002 | Pajunk et al. |
| 2002/0049448 A1 | 4/2002 | Sand et al. |
| 2002/0049449 A1 | 4/2002 | Bhatnagar et al. |
| 2002/0058947 A1 | 5/2002 | Hochschuler et al. |
| 2002/0067658 A1 | 6/2002 | Vendrely et al. |
| 2002/0068939 A1 | 6/2002 | Levy et al. |
| 2002/0068974 A1 | 6/2002 | Kuslich et al. |
| 2002/0068975 A1 | 6/2002 | Teitelbaum et al. |
| 2002/0072768 A1 | 6/2002 | Ginn |
| 2002/0082605 A1 | 6/2002 | Reiley et al. |
| 2002/0099384 A1 | 7/2002 | Scribner et al. |
| 2002/0099385 A1 | 7/2002 | Ralph et al. |
| 2002/0118595 A1 | 8/2002 | Miller |
| 2002/0123716 A1 | 9/2002 | VanDiver et al. |
| 2002/0156483 A1 | 10/2002 | Voellmicke et al. |
| 2002/0161373 A1 | 10/2002 | Osorio et al. |
| 2002/0177866 A1 | 11/2002 | Weikel et al. |
| 2002/0183851 A1 | 12/2002 | Spiegelberg et al. |
| 2002/0188300 A1 | 12/2002 | Arramon et al. |
| 2002/0191487 A1 | 12/2002 | Sand |
| 2003/0009177 A1 | 1/2003 | Middleman et al. |
| 2003/0018339 A1 | 1/2003 | Higueras et al. |
| 2003/0031698 A1 | 2/2003 | Roeder et al. |
| 2003/0032929 A1 | 2/2003 | McGuckin, Jr. |
| 2003/0036763 A1 | 2/2003 | Bhatnagar et al. |
| 2003/0040718 A1 | 2/2003 | Kust et al. |
| 2003/0050644 A1 | 3/2003 | Boucher et al. |
| 2003/0050702 A1 | 3/2003 | Berger |
| 2003/0078589 A1 | 4/2003 | Preissman |
| 2003/0109883 A1 | 6/2003 | Matsuzaki et al. |
| 2003/0109884 A1 | 6/2003 | Tague et al. |
| 2003/0144742 A1 | 7/2003 | King et al. |
| 2003/0162864 A1 | 8/2003 | Pearson et al. |
| 2003/0174576 A1 | 9/2003 | Tague et al. |
| 2003/0181963 A1 | 9/2003 | Pellegrino et al. |
| 2003/0185093 A1 | 10/2003 | Vendrely et al. |
| 2003/0220414 A1 | 11/2003 | Axen et al. |
| 2003/0225364 A1 | 12/2003 | Kraft et al. |
| 2003/0227816 A1 | 12/2003 | Okamoto et al. |
| 2003/0231545 A1 | 12/2003 | Seaton |
| 2004/0010263 A1 | 1/2004 | Boucher et al. |
| 2004/0029996 A1 | 2/2004 | Kuhn |
| 2004/0054377 A1 | 3/2004 | Foster et al. |
| 2004/0059283 A1 | 3/2004 | Kirwan et al. |
| 2004/0066706 A1 | 4/2004 | Barker et al. |
| 2004/0068264 A1 | 4/2004 | Treace |
| 2004/0073139 A1 | 4/2004 | Hirsch et al. |
| 2004/0092946 A1 | 5/2004 | Bagga et al. |
| 2004/0098015 A1 | 5/2004 | Weikel et al. |
| 2004/0106913 A1 | 6/2004 | Eidenschink et al. |
| 2004/0122438 A1 | 6/2004 | Abrams |
| 2004/0132859 A1 | 7/2004 | Puckett, Jr. et al. |
| 2004/0133124 A1 | 7/2004 | Bates et al. |
| 2004/0133211 A1 | 7/2004 | Raskin et al. |
| 2004/0138759 A1 | 7/2004 | Muller et al. |
| 2004/0157952 A1 | 8/2004 | Soffiati et al. |
| 2004/0157954 A1 | 8/2004 | Imai et al. |
| 2004/0162559 A1 | 8/2004 | Arramon et al. |
| 2004/0167532 A1 | 8/2004 | Olson et al. |
| 2004/0167562 A1 | 8/2004 | Osorio et al. |
| 2004/0167625 A1 | 8/2004 | Beyar et al. |
| 2004/0193171 A1 | 9/2004 | DiMauro |
| 2004/0215202 A1 | 10/2004 | Preissman |
| 2004/0220672 A1 | 11/2004 | Shadduck |
| 2004/0226479 A1 | 11/2004 | Lyles et al. |
| 2004/0229972 A1 | 11/2004 | Klee et al. |
| 2004/0230309 A1 | 11/2004 | DiMauro et al. |
| 2004/0236313 A1 | 11/2004 | Klein |
| 2004/0249015 A1 | 12/2004 | Jia et al. |
| 2004/0249347 A1 | 12/2004 | Miller et al. |
| 2004/0260303 A1 | 12/2004 | Carrison |
| 2004/0260304 A1 | 12/2004 | Faccioli et al. |
| 2004/0267154 A1 | 12/2004 | Sutton et al. |
| 2005/0014273 A1 | 1/2005 | Dahm et al. |
| 2005/0015148 A1 | 1/2005 | Jansen et al. |
| 2005/0025622 A1 | 2/2005 | Djeridane et al. |
| 2005/0058717 A1 | 3/2005 | Yetlinler |
| 2005/0060023 A1 | 3/2005 | Mitchell et al. |
| 2005/0070912 A1 | 3/2005 | Voellmicke |
| 2005/0070914 A1 | 3/2005 | Constantz et al. |
| 2005/0070915 A1* | 3/2005 | Mazzuca et al. ............... 606/93 |
| 2005/0083782 A1 | 4/2005 | Gronau et al. |
| 2005/0113762 A1 | 5/2005 | Kay et al. |
| 2005/0143827 A1 | 6/2005 | Globerman et al. |
| 2005/0154081 A1 | 7/2005 | Yin et al. |
| 2005/0159724 A1 | 7/2005 | Enerson |
| 2005/0180806 A1* | 8/2005 | Green et al. ................... 401/119 |
| 2005/0203206 A1 | 9/2005 | Trieu |
| 2005/0209695 A1 | 9/2005 | de Vries et al. |
| 2005/0216025 A1 | 9/2005 | Chern Lin et al. |
| 2005/0256220 A1 | 11/2005 | Lavergne et al. |
| 2005/0281132 A1 | 12/2005 | Armstrong et al. |
| 2006/0035997 A1 | 2/2006 | Orlowski et al. |
| 2006/0041033 A1 | 2/2006 | Bisig et al. |
| 2006/0052794 A1 | 3/2006 | McGill |
| 2006/0074433 A1 | 4/2006 | McGill et al. |
| 2006/0079905 A1 | 4/2006 | Beyar et al. |
| 2006/0116643 A1 | 6/2006 | Dixon et al. |
| 2006/0116689 A1 | 6/2006 | Albans et al. |
| 2006/0116690 A1 | 6/2006 | Pagano |
| 2006/0122614 A1 | 6/2006 | Truckai et al. |
| 2006/0148923 A1 | 7/2006 | Ashman et al. |
| 2006/0167148 A1 | 7/2006 | Engquist et al. |
| 2006/0181959 A1 | 8/2006 | Weiss et al. |
| 2006/0235338 A1 | 10/2006 | Pacheco |
| 2006/0241644 A1 | 10/2006 | Osorio et al. |
| 2006/0264695 A1 | 11/2006 | Viole et al. |
| 2006/0264967 A1 | 11/2006 | Ferreyro et al. |
| 2006/0266372 A1 | 11/2006 | Miller et al. |
| 2006/0271061 A1 | 11/2006 | Beyar et al. |
| 2006/0276819 A1 | 12/2006 | Osorio et al. |
| 2007/0027230 A1 | 2/2007 | Beyar et al. |
| 2007/0032567 A1 | 2/2007 | Beyar et al. |
| 2007/0055266 A1 | 3/2007 | Osorio et al. |
| 2007/0055267 A1 | 3/2007 | Osorio et al. |
| 2007/0055278 A1 | 3/2007 | Osorio et al. |
| 2007/0055280 A1 | 3/2007 | Osorio et al. |
| 2007/0055284 A1 | 3/2007 | Osorio et al. |
| 2007/0055285 A1 | 3/2007 | Osorio |
| 2007/0055300 A1 | 3/2007 | Osorio et al. |
| 2007/0060941 A1 | 3/2007 | Reiley et al. |
| 2007/0118142 A1 | 5/2007 | Krueger |
| 2007/0142842 A1 | 6/2007 | Krueger |
| 2007/0197935 A1 | 8/2007 | Reiley et al. |
| 2007/0198013 A1 | 8/2007 | Foley et al. |
| 2007/0198023 A1 | 8/2007 | Sand et al. |
| 2007/0198024 A1 | 8/2007 | Plishka et al. |
| 2007/0255282 A1 | 11/2007 | Simonton et al. |
| 2007/0282443 A1 | 12/2007 | Globerman et al. |
| 2008/0039856 A1 | 2/2008 | DiMauro |
| 2008/0044374 A1 | 2/2008 | Lavergne et al. |
| 2008/0058827 A1 | 3/2008 | Osorio et al. |
| 2008/0065087 A1 | 3/2008 | Osorio et al. |
| 2008/0065089 A1 | 3/2008 | Osorio et al. |
| 2008/0065137 A1 | 3/2008 | Boucher et al. |
| 2008/0065142 A1 | 3/2008 | Reiley et al. |
| 2008/0065190 A1 | 3/2008 | Osorio et al. |
| 2008/0071283 A1 | 3/2008 | Osorio et al. |
| 2008/0086133 A1 | 4/2008 | Kuslich et al. |
| 2008/0132935 A1 | 6/2008 | Osorio et al. |
| 2008/0140079 A1 | 6/2008 | Osorio et al. |
| 2008/0140084 A1 | 6/2008 | Osorio et al. |
| 2008/0200915 A1 | 8/2008 | Globerman et al. |

(56) References Cited

U.S. PATENT DOCUMENTS

| | | | |
|---|---|---|---|
| 2008/0212405 A1 | 9/2008 | Globerman et al. |
| 2008/0228192 A1 | 9/2008 | Beyar et al. |
| 2009/0264892 A1 | 10/2009 | Beyar et al. |
| 2009/0264942 A1 | 10/2009 | Beyar et al. |
| 2010/0065154 A1 | 3/2010 | Globerman |
| 2010/0069786 A1 | 3/2010 | Globerman |
| 2010/0152855 A1 | 6/2010 | Kuslich et al. |
| 2010/0168271 A1 | 7/2010 | Beyar |
| 2010/0268231 A1 | 10/2010 | Kuslich et al. |
| 2012/0307586 A1 | 12/2012 | Globerman et al. |
| 2013/0123791 A1 | 5/2013 | Beyar et al. |
| 2013/0261217 A1 | 10/2013 | Beyar et al. |
| 2013/0345708 A1 | 12/2013 | Beyar et al. |
| 2014/0088605 A1 | 3/2014 | Ferreyro et al. |
| 2014/0148866 A1 | 5/2014 | Globerman et al. |
| 2015/0122691 A1 | 5/2015 | Globerman et al. |
| 2015/0127058 A1 | 5/2015 | Beyar et al. |
| 2015/0148777 A1 | 5/2015 | Ferreyro et al. |
| 2016/0051302 A1 | 2/2016 | Ferreyro et al. |
| 2016/0235459 A1 | 8/2016 | Globerman et al. |

FOREIGN PATENT DOCUMENTS

| | | |
|---|---|---|
| CN | 1138001 A | 12/1996 |
| CN | 1310026 A | 8/2001 |
| DE | 136018 C | 11/1902 |
| DE | 226956 | 3/1909 |
| DE | 868497 C | 2/1953 |
| DE | 1283448 | 11/1968 |
| DE | 1810799 | 6/1970 |
| DE | 2821785 | 11/1979 |
| DE | 3003947 | 8/1980 |
| DE | 2947875 | 4/1981 |
| DE | 3443167 | 6/1986 |
| DE | 8716073 | 3/1988 |
| DE | 3817101 A1 | 11/1989 |
| DE | 3730298 | 2/1990 |
| DE | 4104092 | 8/1991 |
| DE | 293485 | 9/1991 |
| DE | 4016135 | 3/1992 |
| DE | 4315757 | 11/1994 |
| DE | 19612276 | 10/1997 |
| DE | 10258140 | 7/2004 |
| EP | 20207 | 6/1908 |
| EP | 486638 | 6/1938 |
| EP | 0044877 | 2/1982 |
| EP | 0190504 | 3/1986 |
| EP | 0177781 | 4/1986 |
| EP | 0 235 905 A1 | 9/1987 |
| EP | 0235905 | 9/1987 |
| EP | 0301759 | 7/1988 |
| EP | 0242672 | 9/1989 |
| EP | 0425200 | 10/1990 |
| EP | 0 235 905 B1 | 12/1990 |
| EP | 0423916 | 4/1991 |
| EP | 0475077 | 3/1992 |
| EP | 0511868 | 4/1992 |
| EP | 0493789 | 7/1992 |
| EP | 0581387 | 2/1994 |
| EP | 0 614 653 A2 | 9/1994 |
| EP | 0669100 | 8/1995 |
| EP | 0748615 | 12/1996 |
| EP | 0763348 | 3/1997 |
| EP | 1 074 231 A1 | 2/2001 |
| EP | 1074231 | 2/2001 |
| EP | 1095667 | 5/2001 |
| EP | 1103237 | 5/2001 |
| EP | 1104260 | 6/2001 |
| EP | 1 247 454 A1 | 10/2002 |
| EP | 1464292 | 10/2004 |
| EP | 1 517 655 A1 | 3/2005 |
| EP | 1148850 | 4/2005 |
| EP | 1552797 | 7/2005 |
| EP | 1570873 | 9/2005 |
| EP | 1 596 896 A2 | 11/2005 |
| EP | 1598 015 | 11/2005 |
| EP | 1148851 | 5/2006 |
| EP | 1 829 518 A1 | 9/2007 |
| EP | 1 886 647 A1 | 2/2008 |
| EP | 1 886 648 A1 | 2/2008 |
| FR | 1548575 | 10/1968 |
| FR | 2606282 | 5/1988 |
| FR | 2629337 | 10/1989 |
| FR | 2638972 | 5/1990 |
| FR | 2674119 | 9/1992 |
| FR | 2690332 | 10/1993 |
| FR | 2712486 | 5/1995 |
| FR | 2722679 | 1/1996 |
| GB | 8331 | 0/1904 |
| GB | 179502045 | 4/1795 |
| GB | 190720207 A | 6/1908 |
| GB | 408668 | 4/1934 |
| GB | 486638 A | 6/1938 |
| GB | 2114005 | 8/1983 |
| GB | 2156824 | 10/1985 |
| GB | 2 197 691 A | 5/1988 |
| GB | 2268068 | 1/1994 |
| GB | 2276560 | 10/1994 |
| GB | 2411849 | 9/2005 |
| GB | 2413280 | 10/2005 |
| GB | 2469749 | 10/2010 |
| JP | 51-134465 A | 11/1976 |
| JP | 54-009110 | 1/1979 |
| JP | 55-009242 U | 1/1980 |
| JP | 55-109440 | 8/1980 |
| JP | 62-068893 | 3/1987 |
| JP | 63-194722 A | 8/1988 |
| JP | 02-122017 | 5/1990 |
| JP | 02-166235 | 6/1990 |
| JP | 02-125730 U | 10/1990 |
| JP | 04-329956 A | 11/1992 |
| JP | 07-000410 | 1/1995 |
| JP | 8322848 | 12/1996 |
| JP | 10146559 | 6/1998 |
| JP | 10-511569 | 10/1998 |
| JP | 2001-514922 A | 9/2001 |
| JP | 2004-16707 | 1/2004 |
| JP | 2005-500103 A | 1/2005 |
| JP | 2008-55367 | 3/2008 |
| RO | 116784 | 6/2001 |
| RU | 662082 | 5/1979 |
| RU | 1011119 | 4/1983 |
| RU | 1049050 | 10/1983 |
| WO | 88/10129 A1 | 12/1988 |
| WO | WO 90/00037 | 1/1990 |
| WO | WO 92/14423 | 9/1992 |
| WO | WO 94/12112 | 6/1994 |
| WO | WO 95/13862 | 5/1995 |
| WO | WO 96/11643 | 4/1996 |
| WO | WO 96/19940 | 7/1996 |
| WO | WO 96/32899 | 10/1996 |
| WO | WO 96/37170 | 11/1996 |
| WO | WO 97/18769 | 5/1997 |
| WO | WO 97/28835 | 8/1997 |
| WO | WO 98/28035 | 7/1998 |
| WO | WO 98/38918 | 9/1998 |
| WO | WO 99/18866 | 4/1999 |
| WO | WO 99/18894 | 4/1999 |
| WO | WO 99/29253 | 6/1999 |
| WO | WO 99/37212 | 7/1999 |
| WO | WO 99/39661 | 8/1999 |
| WO | WO 99/49819 | 10/1999 |
| WO | WO 99/52446 | 10/1999 |
| WO | WO 00/06216 | 2/2000 |
| WO | WO 00/44319 | 8/2000 |
| WO | WO 00/44321 | 8/2000 |
| WO | WO 00/44946 | 8/2000 |
| WO | WO 00/54705 | 9/2000 |
| WO | WO 00/56254 | 9/2000 |
| WO | WO 01/08571 | 2/2001 |
| WO | WO 01/13822 | 3/2001 |
| WO | WO 01/54598 | 8/2001 |
| WO | WO 01/60270 | 8/2001 |
| WO | WO 01/76514 | 10/2001 |

(56) References Cited

FOREIGN PATENT DOCUMENTS

| | | |
|---|---|---|
| WO | WO 02/00143 | 1/2002 |
| WO | WO 02/02033 | 1/2002 |
| WO | WO 02/19933 | 3/2002 |
| WO | 02/064195 A2 | 8/2002 |
| WO | WO 02/064062 | 8/2002 |
| WO | WO 02/064194 | 8/2002 |
| WO | WO 02/072156 | 9/2002 |
| WO | WO 02/096474 | 12/2002 |
| WO | WO 03/007854 | 1/2003 |
| WO | WO 03/015845 | 2/2003 |
| WO | WO 03/022165 | 3/2003 |
| WO | WO 03/061495 | 7/2003 |
| WO | WO 03/078041 | 9/2003 |
| WO | WO 03/101596 | 12/2003 |
| WO | WO 2004/002375 | 1/2004 |
| WO | WO 2004/019810 | 3/2004 |
| WO | WO 2004/071543 | 8/2004 |
| WO | 2004/080357 | 9/2004 |
| WO | WO 2004/075965 | 9/2004 |
| WO | WO 2004/080357 | 9/2004 |
| WO | WO 2004/110292 | 12/2004 |
| WO | WO 2004/110300 | 12/2004 |
| WO | WO 2005/000138 | 1/2005 |
| WO | 2005/017000 A1 | 2/2005 |
| WO | WO 2005/032326 | 4/2005 |
| WO | WO 2005/048867 | 6/2005 |
| WO | WO 2005/051212 | 6/2005 |
| WO | WO 2005/110259 | 11/2005 |
| WO | WO 2006/011152 | 2/2006 |
| WO | WO 2006/039159 | 4/2006 |
| WO | 2006/062939 A2 | 6/2006 |
| WO | WO 2006/090379 | 8/2006 |
| WO | WO 2007/015202 | 2/2007 |
| WO | WO 2007/036815 | 4/2007 |
| WO | WO 2007/148336 | 12/2007 |
| WO | WO 2008/004229 | 1/2008 |
| WO | WO 2008/032322 | 3/2008 |
| WO | WO 2008/047371 | 4/2008 |

OTHER PUBLICATIONS

Avalione & Baumeister III, Marks' Standard Handbook for Mechanical Engineers, 10 ed, pp. 5-6 (1996).
Blinc, A et al., "Methyl-methacrylate bone cement surface does not promote platelet aggregation or plasma coagulation in vitro," Thrombosis Research 114:179-84 (2004).
Bohner, M. et al., "Theoretical and Experimental Model to Describe the Injection of a Polymethacrylate Cement into a Porous Structure," Biomaterials 24(16):2721-30 (2003).
Breusch, S. et al., "Knochenzemente auf Basis von Polymethylmethacrylat," Orthopade 32:41-50 (2003) w/ abs.
Canale et al., "Campbell's operative orthopaedic—vol. 3—ninth ed", Mosby:P2097,2121,2184-85,2890-96, (1998) abstracts.
Carrodegus et al., "Injectable Acrylic Bone Cements for Vertebroplasty wi h Improved Properties," J. Biomed. Materials Res. 68(1):94-104 (Jan. 2004).
Cole et al., "AIM Titanium Humeral Nail System," Surgical Technique. DePuy Orthopaedics 17P (2000).
Edeland, "Some additional suggestions for an intervertebral disc prothesis," J. Biomed. Eng. XP008072822, 7(1):57-62 (1985.
European Search Report, from EP05763930.4; dated Sep. 11, 2008.
European Search Report, from EP09151379.6, dated Oct. 20, 2009.
European Search Report, from EP06780252.0, dated Oct. 29, 2009.
Farrar, D.F. et al., "Rheological Properties of PMMA Bone Cements During Curing," Biomaterials 22:3005-13 (2001).
Gheduzzi, S. et al., "Mechanical Characterisation of Three Percutaneous Vertebroplasty Biomaterials," J. Mater Sci Mater Med 17(5):421-26 (2006).
Giannitsios, D. et al., "High Cement Viscosity Reduces Leakage Risk in Vertebroplasty," European Cells & Mat. 10 supp. 3:54 (2005).
Hasenwinkel, J. et al., "A Novel High-Viscosity, Two-Solution Acrylic Bone Cement: Effect of Chemical Composition on Properties," J. Biomed. Materials Research 47(1):36-45 (1999).
Hasenwinkel, J. et al., "Effect of Initiation Chemistry on the Fracture Toughness, Fatigue Strength, and Residual Monomer Content of a Novel High-Viscosity, Two-Solution Acrylic Bone Cement," J. Biomed. Materials Res. 59(3):411-21 (2001).
Heraeus Palacos R, 2008, Palacos R, high Viscosity Bone Cement.
Hernandez et al., "Influence of Powder Particle Size Distribution on Complex Viscosity and Other Properties of Acrylic Bone Cement for Vertebroplasty and Kyphoplasty," J. Biomed. Mat. Res. 77B:98-103 (2006).
International Preliminary Report on Patentability, from PCT/IB06/053014, dated Apr. 10, 2008
International Search Report, from PCT/IL06/00239, dated Jan. 26, 2007.
International Search Report, from PCT/IL05/00812, dated Feb. 28, 2007.
International Search Report, from PCT/IB06/052612, dated Oct. 2, 2007.
International Search Report, from PCT/IL07,00833, dated Apr. 4, 2008.
International Search Report, from PCT/IL07/00484, dated Apr. 17, 2008.
Ishikawa et al., "Effects of Neutral Sodium Hydrogen Phosphate on Setting Reaction and Mechanical Strength of Hydroxyapatite Putty," J. Biomed. Mat. Res. 44:322-29 (199).
Ishikawa et al., "Non-Decay Type Fast-Setting Calcium Phosphate Cement: Hydroxyapatite Putty Containing an Increased Amount of Sodium Alginate," J. Biomed. Mat. Res. 36:393-99 (1997).
Krause et al., "The Viscosity of Acrylic Bone Cements," J. Biomed. Mat. Res. 16:219-43 (1982).
Lewis, "Properties of Acrylic Bone Cement: State of the Art Review," J. Biomed. Mat. Res. Appl. Biomaterials 38(2):155-82 (p. 158 s.Viscosity) (1997).
Lewis, G. et al., "Rheological Properties of Acrylic Bone Cement During Curing and the Role of the Size of the Powder Particles," J. Biomed. Mat. Res. Appl. Biomat. 63(2):191-99 (2002).
Lewis, "Toward Standardization of Methods of Determination of Fracture Properties of Acrylic Bone Cement and Statistical Analysis of Test Results," J. Biomed. Research: Appl. Biomaterials 53(6):748-68 (2000).
Li, C. et al., "Thermal Characterization of PMMA-Based Bone Cement Curing," J. Materials Sci.: Materials in Medicine 15:84-89 (2004).
Lieberman, I.H. et al., "Initial Outcome and Efficacy of Kyphoplasty in the Treatment of Painful Osteoporatic Vertebral Compression Fractures," Spine 26(14:1631-38 (2001).
Mathis, John et al., "Percutaneous Vertebroplasty: A Developing Standard of Care for Vertebral Compression Fractures," AJNR Am. J. Neurorad. 22:373-81 (2001).
Medsafe Palacos R 2007, Data Sheet : Palacos R Bone cement with Garamycin pp. 1-7; http://www.medsafe.govt.nz/profs/datasheet/p/palacosbonecements.htm.
Mousa, W.F. et al., "Biological and Mechanical Properties of PMMA-Based Bioactive Bone Cements," Biomaterials 21:2137-46 (2000).
Nussbaum et al., "The Chemistry of Acrylic Bone Cements and Implications for Clinical Use in Image-Guided Therapy," J. Vasc. Interv. Radiol. 15:121-26 (2004).
Odian, G., "Principles of Polymerization," pp. 20-23.
Pascual, B. et al., "New Aspects of the Effect of Size and Size Distribution on the Setting Parameters and Mechanical Properties of Acrylic Bone Cements," Biomaterials 17(5):509-16 (1996).
Rimnac, CM, et al., "The effect of centrifugation on the fracture properties of acrylic bone cements," JB&JS 68A(2):281-87 (1986).
Robinson, R. et al., "Mechanical Properties of Poly(methyl methacrylate) Bone Cement," J. Biomed. Materials Res. 15(2):203-08 (2004).
Saha, S. et a., "Mechanical Properties of Bone Cement: A Review," J. Biomed. Materials Res. 18(4):435-62 (1984).

(56) References Cited

OTHER PUBLICATIONS

Serbetci, K. et al., "Thermal and Mechanical Properties of Hydroxyapatite Impregnated Acrylic Bone Cements," Polymer Testing 23:145-55 (2004).
Steen, "Laser Surface Treatment," Laser Mat. Processing, Springer 2d ed. ch. 6:218-71 (2003).
Supp. EP Search Report, from EP Appl. No. 05763930.4, dated Sep. 11, 2008.
Supp. EP Search Report, from EP Appl. No. 06711221.9, dated Sep. 15, 2008.
Varela et al., "Closed Intramedullary Pinning of Metacarpal and Phalanx Fractures," Orthopaedics 13(2):213-15 (1990).
Weissman et al., "Trochanteric Fractures of the Femur Treatment with a Strong Nail and Early Weight-Bearing," Clin. Ortho. & Related Res. 67:143-50 (1969).
Zapalowicz, K. et al., "Percutaneous Vertebroplasty with Bone Cement in the Treatment of Osteoporotic Vertebral Compression Fractures," Ortopedia Traumatologia Rehabilitacja NR Jan. 2003.
Codman & Shurtleff, "V-MAX™ Mixing and Delivery Device," Catalog No. 43-1056.
Fessler, Richard D. et al., "Vertebroplasty," Neurosurgical Operative Atlas 9:233-240 (2000).
Jensen, Mary E. et al., "Percutaneous Vertebroplasty in the Treatment of Osteoporotic Compression Fractures," Spine Interventions 10(3):547-568 (2000).
Al-Assir, et al., "Percutaneous Vertebroplasty: A Special Syringe for Cement Injection," AJNR Am. J. Neuroradiol. 21:159-61 (Jan. 2000).
Amar, Arun P. et al., "Percutaneous Transpedicular Polymethylmethacrylate Vertebroplasty for the Treatment of Spinal Compression Fractures," Neurosurgery 49(5):1105-15 (2001).
Baroud, G. et al., "Injection Biomechanics of Bone Cements Used in Vertebroplasty," Biomaterials & Eng. 00:1-18 (2004).
Barr, J.D., "Percutaneous Vertebroplasty for pain Relief and Spinal Stabilization," Spine 25(8):923-28 (2000).
Belkoff, S. et al., The Biomechanics of Vertebroplasty, the Effect of Cement Volume on Mechanical Behavior, SPINE 26(14):1537-41 (2001).
Belkoff, S.M. et al., "An Ex Vivo Biomechanical Evaluation of a Hydroxyapatite Cement for Use with Kyphoplasty," Am. J. Neurorad. 22:1212-16 (2001).
Belkoff, S.M. et al., "An Ex Vivo Biomechanical Evaluation of a Inflatable Bone Tamp Used in the Treatment of Compression Fracture," SPINE 26(2):151-56 (2001).
Belkoff, S.M. et al., "An in Vitro Biomechanical Evaluation of Bone Cements Used in Percutaneous Vertebroplasty," Bone 25(2):23S-26S (1999).
Combs, S. et al., "The Effects of Barium Sulfate on the Polymerization Temperature and Shear Strength of Surgical Simplex P," Clin. Ortho. and Related Res. pp. 287-291 (Jun. 4, 1979).
Cotton, A. et al., "Percutaneous Vertebroplasty: State of the Art," Scientific Exhibit, Radiographics 18:311-20 (1998).
Dean, J.R. et al., "The Strengthening Effect of Percutaneous Vertebroplasty," Clin Radiol. 55:471-76 (2000).
Deramond, H. et al, "Percutaneous Vertebroplasty with Polymethylmethacrylate, Technique Indications and Results," Radiologic Clinics of North America 36(3) (May 1988).
Deramond, H. et al., "Temperature Elevation Caused by Bone cement Polymerization During Vertbroplasty," Bone 25(2):17S-21S (1999).
DeWijn, J.R., Characterization of Bone Cements, The Institute of Dental Materials Science and Technology and the Dept of Ortho., Catholic University, Netherlands 46:38-51 (1975).
Gangi, A., "CT-Guided Interventional Procedures for Pain Management in the Lumbosacral Spine," Radiographics 18:621-33 (1998).
Gangi, A., "Computed Tomography CT and Fluoroscopy-Guided Vertebroplasty: Results and Complications in 187 Patients," Seminars in Interventional Radiology 16(2):137-42 (1999).
Gangi, A., "Percutaneous Vertebroplasty Guided by a Combination of CT and Fluoroscopy," AJNR 15:83-86 (1994).

Garfin, S. R. et al., "New Technologies in Spine, Kyphoplasty and Vertebroplasty for the Treatment of Painful Osteoporotic Compression Fractures," Spine 26(14:1511-15 (2001).
Grados F. et al.,"Long-Term Observations of Vertebral Osteoporotic Fractures Treated by Percutaneous Vertebroplasty," Rheumatology 39:1410-14 (2000).
Heini, P. et al., "Augmentation of Mechanical Properties in Osteoporatic Vertebral Bones—a Biomechanical Investigation of Vertebroplasty Efficacy With Different Bone Cements," EUR Spine J. v. 10, pp. 164-171, Springer-Verlag (2001).
Heini, P., "Percutaneous Transpedicular Vertebroplasty with PMMA: Operative Technique and Early Results," EUR Spine J. v. 9, pp. 445-450, Springer-Verlag (2000).
Heini, P., "The Use of a Side-Opening Injection Cannula in Vertebroplasty," Spine 27(1):105-09 (2002).
International Search Report, for PCT/MX03/000027, filed Mar. 14, 2003.
Jasper, L.E. et al., "The Effect of Monomer-to-Powder Ratio on the Material Properties of Cranioplastic," Bone 25(2):27S-29S (1999).
Jensen, Mary E. et al., "Percutaneous Polymethylmethacrylate Vertebroplasty in the Treatment of Osteoporotic Vertebral Body Compression Fractures: Technical Aspects," AJNR 18:1897-1904 (1997).
Johnson & Johnson Orthopaedics, The CEMVAC Method, Raynham, MA.
Kallmes, D. et al., "Radiation Dose to the Operator During Vertebroplasty: Prospective Comparison of the Use of 1-cc Syringes Versus an Injection Device," AJNR Am. J. Neuroradiol. 24:1257-60 (2003).
Kaufmann et al, "Age of Fracture and Clinical Outcomes of Percutaneous Vertebroplasty," Am. J. Neuroradiology 22:1860-63 (2001).
Kuhn, Klaus-Dieter, Bone Cements—Uptodate Comparison of Physical and Chemical Properties of Commercial Materials, Springer-Verlag Heidelberg Germany (2000).
Kyphom Medical Professionals, KyphXProducts (Nov. 8, 2001).
O'Brien, J. et al., "Vertebroplasty in patients with Severe Vertebral Compression Fractures: A Technical Report," AJNR 21:1555-58 (2000).
Padovani, B. et al., "Pulmonary Embolism Caused by Acrylic Cement: A Rare Complication of Percutaneous Vertebroplasty," AJNR 20:375-77 (1999).
Parallax Medical, Inc., Exflow Cement Delivery System (May 16, 2000).
Ryu, K. S. et al., "Dose-Dependent Epidural Leakage of Polymethylmethacrylate after Percutaneous Vertebroplasty in Patients with Osteoporotic Vertebral Compression Fractures," J. Neuro: Spine 96:56-61 (2002).
Shah, T., Radiopaque Polymer Formulations for Medical Devices; Medical Plastics and Biomaterials Special Section; Medical device & Diagnostic Industry pp. 102-111 (2000).
Vasconcelos, C., "Transient Arterial Hypotension Induced by Polymethyacrylated Injection During Percutaneous Vertebroplasty," Letter to the Editor, JVIR (Aug. 2001).
Wimhurst, J.A., et al., "The Effects of Particulate Bone Cements at the Bone-Implant Interface," J. Bone & Joint Surgery pp. 588-592 (2001).
Wimhurst, J.A. et al., "Inflammatory Responses of Human Primary Macrophages to Particulate Bone Cements in Vitro," J. Bone & Joint Surgery 836:278-82 (2001).
U.S. Office Action from corresponding U.S. Appl No. 10/405,113, dated Jul. 27, 2009.
Feldman, H., "Die Geschichte der Injektionen," Laryngo-Rhino-Othol 79:239-46 (2000).
Glasgow Medico-Chirurgical Society, The lancet 1364 (May 18, 1907).
Greenberg, "Filling Root Canals by an Injection Technique," Dental Digest 61-63 (Feb. 1963).
Greenberg, "Filling Root Canals in Deciduous Teeth by an Injection Technique," Dental Digest 574-575 (Dec. 1961).
Greig, D., "A New Syringe for Injecting Paraffin," The Lancet 611-12 (Aug. 29, 1903).

(56) References Cited

OTHER PUBLICATIONS

Lake, R., "The Restoration of the Inferior Turbinate Body by Paraffin Injections in the Treatment of Atrophic Rhinitis," The Lancet 168-69 (Jan. 17, 1903).
Paget, S., "The Uses of Paraffin in Plastic Surgery," The Lancet 1354 (May 16, 1903).
Walton, A, "Some Cases of Bone Cavities Treated by Stopping With Paraffin," The Lancet 155 (Jan. 18, 1908).
International Search Report, from corresponding PCT/IL07/01257, dated Jul. 15, 2008.
Cromer, A., "Fluids," Physics for the Life Sciences, 2:136-37 (1977).
International Search Report, for PCT/IL07/00808, dated Aug. 22, 2008.
JP Office Action, from JP Appl No. 2008-532910, dated Jul. 19, 2011.
JP Office Action, from JP Appl No. 2009-517607, dated Aug. 9, 2011.
Lindeburg, M., "External Pressurized Liquids," Mechanical Eng. Ref. Manual for the PE Exam, 10:15-14(May 1997).
Marks, Standard handbook for mechanical engineers, section 5 (Tenth ed. 1996).
Supp. EP Search Report, from EP 07766838.2, dated May 18, 2011.
Baroud, G., "Influence of Mixing Method on the Cement Temperature-Mixing Time History and Doughing Time of Three Acrylic Cements for Vertebroplasty," Wiley Periodicals Inc. 112-116 (2003).
European Search Report, from EP 10182769.9, dated Mar. 2, 2011.
European Search Report, from EP 10182693.1, dated Mar. 2, 2011.
European Search Report, from EP 10192302.7, dated Mar. 24, 2011.
European Search Report, from EP 10192301.9, dated Mar. 24, 2011.
European Search Report, from EP 10192300.1, dated Mar. 24, 2011.
Hide, I. et al., "Percutaneous Vertebroplasty: History, Technique and current Perspectives," Clin. Radiology 59:461-67 (2004).
Hu, M. et al., "Kyphoplasty for Vertebral Compression Fracture Via a Uni-Pedicular Approach," Pain Phys. 8:363-67 (2005).
Liang, B. et al., "Preliminary Clinical Application of Percutaneous Vertebroplasty," Zhong Nan Da Xue Bao Yi Xue Ban 31(1):114-9 (2006)(abs. only).
Noetzel, J. et al., Calcium Phosphate Cements in Medicine and Denistry—A Review of Literature, Schweiz Monatsschr Zehmed 115(12):1148-56 (2005)(abs. only).
Supp. EP Search Report, from EP Appl. No. 07766863.0, dated Apr. 12, 2011.
[No Author Listed] Simplex P Bone Cement. Stryker Corporation, 2 pages, publication date unknown. Retrieved from <http://www.stryker.com/en-us/products/Orthopaedics/BoneCementSubstitutes/index.htm>.
[No Author Listed] Standard Specification for Acrylic Bone Cement. Designation F 451-08, ASTM International (2008), 11 pages.
Australian Office Action dated Mar. 7, 2013 for Application No. 2012203300 (6 pages).
Chinese Office Action for Application No. 201310064546.9, dated Jul. 31, 2014 (24 pages).
European Communication dated Jul. 1, 2015 for Application No. 10182769.9, enclosing third party observations concerning patentability (Submission dated Jun. 25, 2015) (6 pages).
Notice of Opposition to a European Patent for Patent No. 2314259, from KIPA AB (EP Application No. 10182769.9), dated Apr. 28, 2016 (72 pages).
Notice of Opposition to a European Patent for Patent No. 2314259, from LOYER & ABELLO (EP Application No. 10182769.9), dated Apr. 28, 2016 (40 pages).
European Communication for Application No. 10192301.9, dated Sep. 17, 2015, enclosing third party observations concerning patentability (Submission dated Sep. 11, 2015 (22 pages).
European Search Report for Application No. 12181745.6, dated Sep. 25, 2012. (9 pages).
European Search Report for Application No. 13174874.1, dated Nov. 13, 2013 (6 pages).
Extended European Search Report for Application No. 14166420.1, dated Jul. 14, 2014 (9 pages).
Extended European Search Report for Application No. 16173186.4, dated Oct. 6, 2016 (11 pages).
Japanese Office Action dated Apr. 9, 2013 for Application No. 2007-556708.
Japanese Office Action for Application No. 2009-516062, dated Oct. 16, 2012 (6 pages).
Japanese Interrogation for Application No. 2009-516062 (Appeal No. 2013-002371) dated Jul. 9, 2013 (9 pages).
Japanese Office Action for Application No. 2009-517607, dated Aug. 28, 2012. (4 pages).
Japanese Office Action for Application No. 2009-517607, dated Aug. 27, 2013. (6 pages).
Japanese Office Action for Application No. 2009-517607, dated Feb. 4, 2014. (8 pages).
Juneja, BL, Plastic Deformation of Metals and Related Properties. Chapter 1. New Age International. p. 1-29, 2010.
Kuehn et al., Acrylic bone cements: composition and properties. Orthop Clin North Am. Jan. 2005;36(1):17-28, v.
Lu Orthopedic Bone Cement. Biomechanics and Biomaterials in Orthopedics. Ed. Poitout London: Springer-Verlag London Limited Jul. 2004 86-88.
Su, W.-F, Polymer Size and Polymer Solutions. Principles of Polymer Design and Synthesis. Chapter 2, pp. 9-26, Springer-Verlag Berlin Heidelberg, 2013.
European Search Report, from EP07827231.7, dated Sep. 12, 2011.
Japanese Office Action dated Dec. 6, 2011 for Application No. 2008-524651 (9 pages).
Japanese Office Action dated Feb. 21, 2012 for Application No. 2009-516062 (6 pages).
Mendizabal et al., Modeling of the curing kinetics of an acrylic bone cement modified with hydroxyapatite. International Journal of Polymeric Materials. 2003;52:927-938.
Morejon et al., Kinetic effect of hydroxyapatite types on the polymerization of acrylic bone cements. International Journal of Polymeric Materials. 2003;52(7):637-654.
Sreeja et al., Studies on poly(methyl methacrylate)lpolystyrene copolymers for potential bone cement applications. Metals Materials and Processes. 1996;8(4):315-322.
Yang et al., Polymerization of acrylic bone cement investigated by differential scanning calorimetry: Effects of heating rate and TCP content. Polymer Engineering and Science. Jul. 1997;1182-1187.

* cited by examiner

REMOTELY-ACTIVATED VERTEBROPLASTY INJECTION DEVICE

RELATED APPLICATIONS

This application is a continuation of U.S. patent application Ser. No. 10/405,113 to DiMauro et al., filed on Mar. 31, 2003, and entitled "Remotely-Activated Vertebroplasty Injection Device," which application is incorporated herein by reference in its entirety.

BACKGROUND OF THE INVENTION

Over 700,000 vertebral fractures occur each year in the United States. Eighty-five percent of these vertebral fractures are associated with osteoporosis. Osteoporosis causes bone to lose density and strength resulting in porous, weak bones especially susceptible to fracture.

Vertebroplasty is a non-surgical procedure for combating the effects of osteoporosis and the like, in which a vertebral body is structurally reinforced using a special cement-like substance, or bone cement. A typical bone cement for use in vertebroplasty is called "polymethylmethacrylate acrylic cement" (PMMA). Vertebroplasty has been used in the treatment of vertebral lesions (hemangoma), spreadable tumors of the spine (e.g. cancer), and osteoporotic vertebral fracture.

When performing vertebroplasty, the clinician uses fluoroscopy for needle placement and for monitoring the injection of bone cement within the vertebral body. Using a simple syringe, the clinician is exposed to excessive x-ray radiation within a fluoro field produced by a fluoroscope. It is well known that excessive exposure to x-ray radiation is dangerous and even cancer-causing. Thus, in order to reduce such exposure, the clinician should perform this procedure outside the range of the fluoro field.

Known techniques for keeping the clinician outside of the fluoro field typically involve the use of a long extension tube, whereby one end of the tube extends from an injection pump and the other end is coupled to a hollow bone needle. The extension tube is used as a conduit for delivering the bone cement from the pump to the bone needle for injection into the vertebral body. The additional length of the extension tube allows a clinician to perform the vertebroplasty at a distance outside the fluoro field.

A disadvantage of such injection devices is that the extension tube produces a pressure drop, making it more difficult to deliver the bone cement through the tube. Mechanisms can be implemented to increase the pressure for pushing the cement through the tube. However, such mechanisms typically reduce the natural feedback or "feel" of the injection device, resulting in a number of pressure concerns. For example, the lack of natural feedback can cause the clinician to inadvertently leak bone cement into the surrounding tissue or the spinal cord itself, resulting in a number of serious health risks. Furthermore, the additional length of the tube makes such injection devices susceptible to premature curing or hardening, resulting in the tube becoming clogged.

SUMMARY OF THE INVENTION

The present invention is directed to a device for remotely injecting a fluorescent probe material into a patient. The flourescent probe material can include, for example, a mixture of a bone cement (e.g., PMMA) and a flourescent probe (e.g., barium, tantalum). Embodiments of the invention include a pump defining an injection chamber having an exit opening, an actuator, and a cable. Although not so limited, the cable can be a tensile flexible cable or a rigid rod. The cable has a first end coupled to the actuator and a second end engaging the pump. The actuator controls the pump by responsive movement of the cable, causing injection of the fluorescent probe material from the injection chamber through the exit opening into the patient.

Particular embodiments of the invention include a pump, having a piston disposed within an inner surface of the injection chamber and a piston driver engaging the piston to allow axial movement of the piston along a first axis defined by first and second end portions of the injection chamber. The second end of the cable engages the piston driver such that the actuator can control the piston driver by responsive movement of the cable, thereby causing axial movement of the piston toward the exit opening of the injection chamber. The piston driver can include gear and pulley mechanisms. The piston driver can also include a lever, thereby providing a mechanical advantage in applying a force to the piston. In alternative embodiments, the piston driver may also include hydraulic cylinders or air cylinders.

In operation, an injection pump is anchored to the patient and a hollow bone needle extends from the exit opening of the pump for transferring the fluorescent probe material into the vertebral body of the patient. The needle can be straight or angled. By anchoring the pump directly to the patient, problems typically associated with extension tubes are eliminated.

Such embodiments improve clinician safety because the pump is remotely operated at a safe distance outside the range of the fluoro field. Furthermore, the pump can be anchored directly to the patient, thereby avoiding the use of extension tubes and thereby improving control and reducing pressure concerns.

DETAILED DESCRIPTION OF THE INVENTION

Figure 1A:
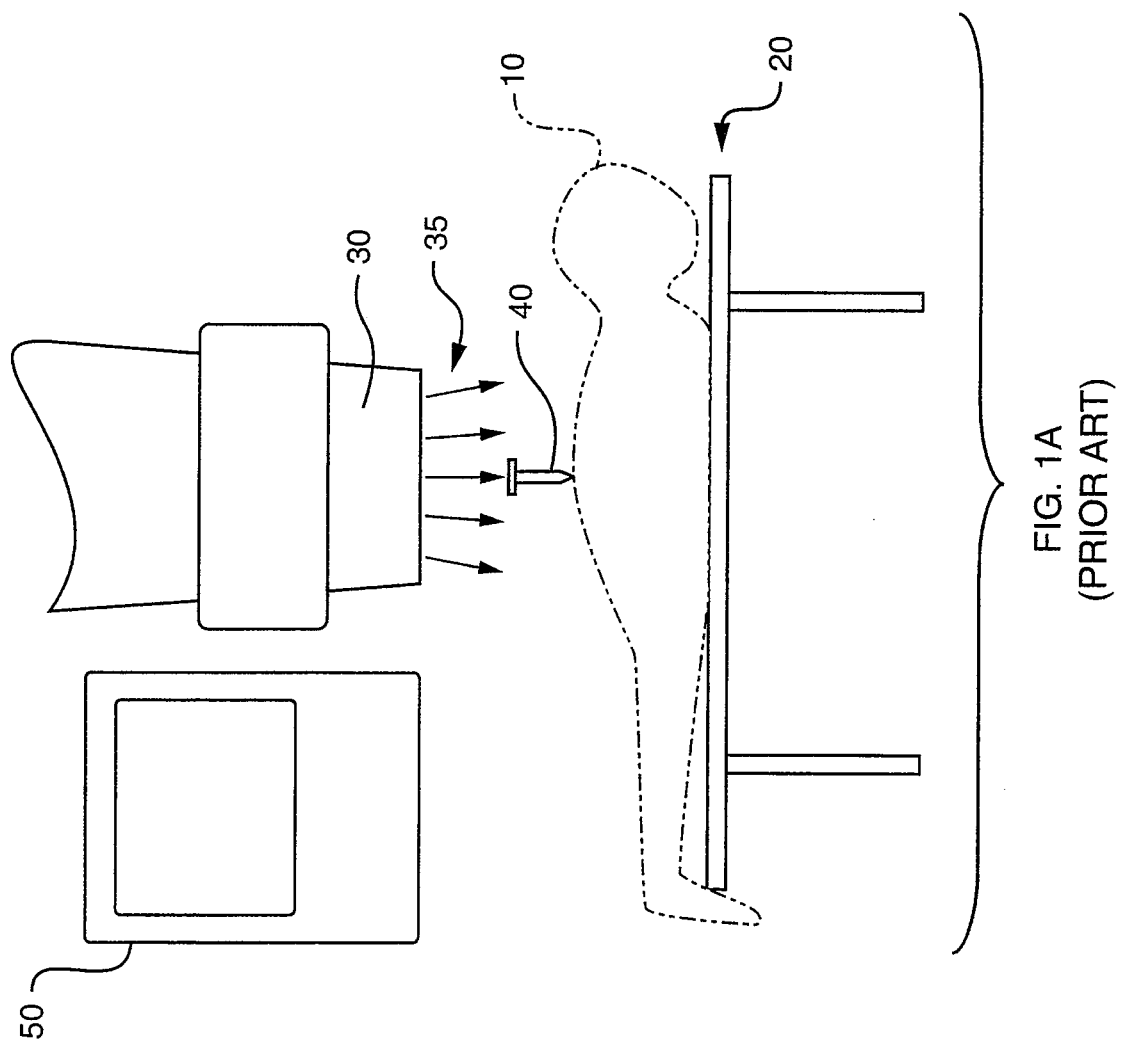
FIG. 1A is a diagram illustrating a general prior art procedure for performing vertebroplasty.

The foregoing and other objects, features and advantages of the invention will be apparent from the following more particular description of preferred embodiments of the invention, as illustrated in the accompanying drawings in which like reference characters refer to the same parts throughout the different views. The same number present in different drawings refers to the same item. The drawings are not necessarily to scale, emphasis instead being placed upon illustrating the principles of the invention.

FIG. 1A is a diagram illustrating a general procedure for performing vertebroplasty. In this procedure, anesthetized patient 10 lies on operating table 20 in a downward-facing, horizontal position underneath x-ray machine 30, referred to as a fluoroscope.

Figure 1B:
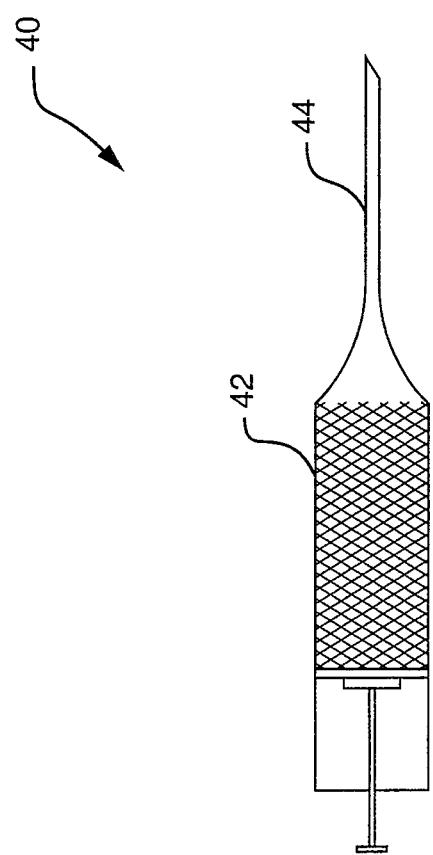
FIG. 1B is a representation of a prior art device for injecting a fluorescent probe material into a patient during vertebroplasty.

The clinician mixes the bone cement along with a flourescent probe to the consistency of a thin paste and prepares the resulting flourescent probe material for injection into the vertebral body through syringe 40, which is also shown in FIG. 1B. Flourescent probe material 42 can be barium, tantalum or other injectable substance that is visible under fluoroscopy. With fluoroscopy, the clinician is able to view the flourescent probe as it is injected into the patient and thereby control the injection process.

Fluoroscopy is a technique for obtaining "live" x-ray images of a patient. X-rays 35, represented in FIG. 1A, are transmitted from fluoroscope 30 through patient 10, striking a flourescent plate. The flourescent plate is coupled to an image intensifier, which is further coupled to a video camera. The camera, in turn, provides a live video feed to video monitor 50, highlighting the flourescent probe within patient 10.

Using video monitor 50 as a visual guide, the clinician positions hollow bone needle 44, shown in FIG. 1B, into the vertebral body in the patient's back and proceeds to inject the flourescent material. After injecting the bone cement, the cement hardens resulting in the stabilization of the vertebral body.

Figure 2:
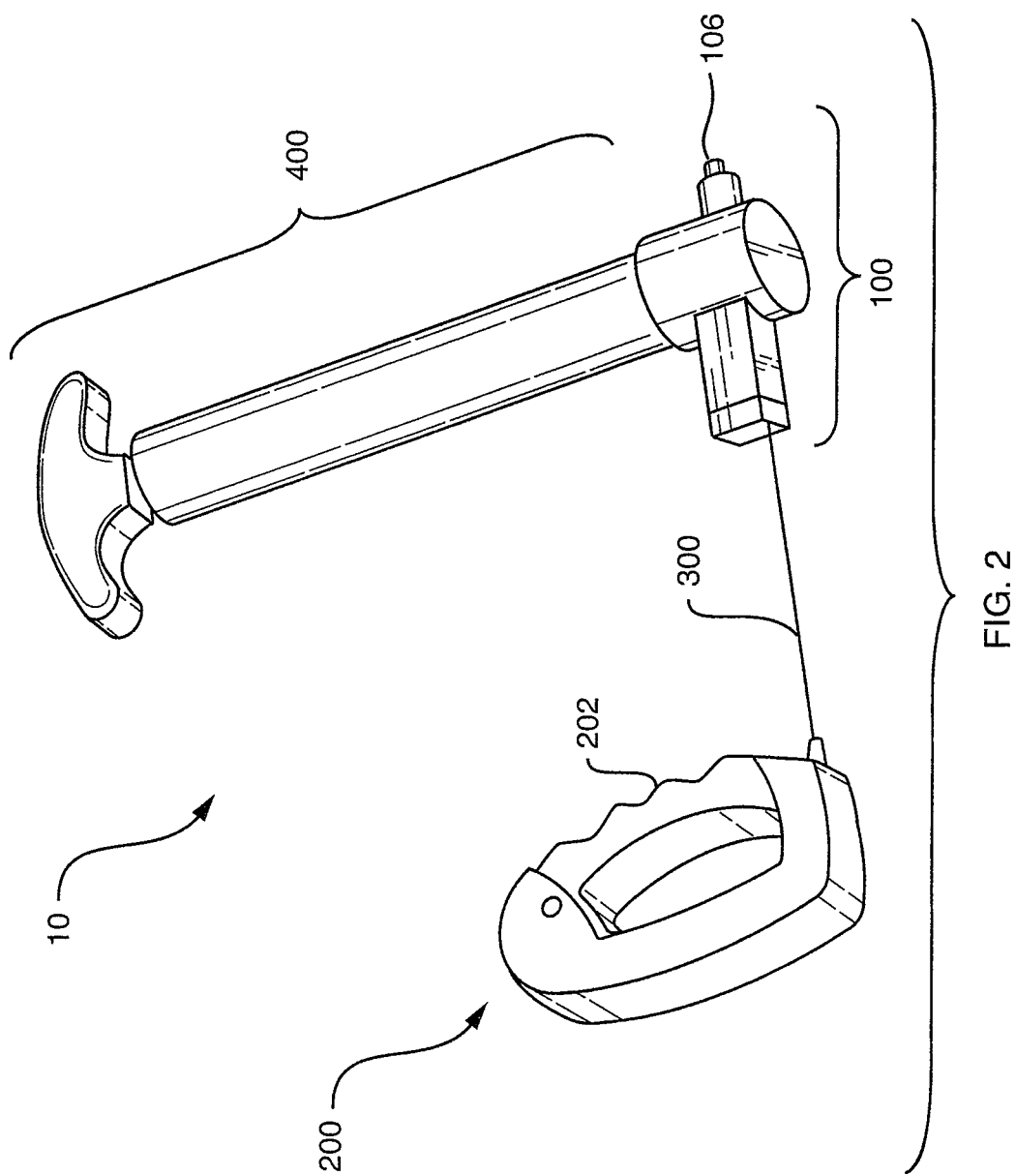
FIG. 2 is a diagram of a remotely-activated vertebroplasty injection device according to one embodiment of the invention.

FIG. 2 is a diagram of a remotely-activated vertebroplasty injection device according to one embodiment of the invention. Injection device 10 includes injection pump 100 that is coupled to actuator 200 by cable 300 having a sufficient length to allow a clinician to operate pump 100 at a distance outside the range of the harmful fluoro field. For example, the cable can have a length of between about one (1) foot and about ten (10) feet, preferably at least two (2) feet, more preferably at least five (5) feet. Actuator 200 controls pump 100 by trigger 202, which causes responsive movement of cable 300, thereby injecting the fluorescent probe material from pump 100 through exit opening 106.

In operation, injection pump 100 is anchored to the patient and a hollow bone needle (not shown) extends from exit opening 106 of pump 100 for transferring the fluorescent probe material into the vertebral body of the patient. By anchoring pump 100 directly to the patient, problems typically associated with extension tubes are eliminated.

Remotely-activated injection device 10 can optionally include reservoir 400 for mixing bone cement (e.g., PMMA) and fluorescent probe (e.g., barium, tantalum) and for supplying the resulting fluorescent probe material to the injection chamber of injection pump 100. For more details regarding the reservoir and a particular bone cement, refer to U.S. Patent Application Publication US2002/0156483 entitled "Vertebroplasty Injection Device and Bone Cement Therefor," filed Feb. 15, 2001, the entire teachings of which are incorporated herein by reference.

Figure 3:
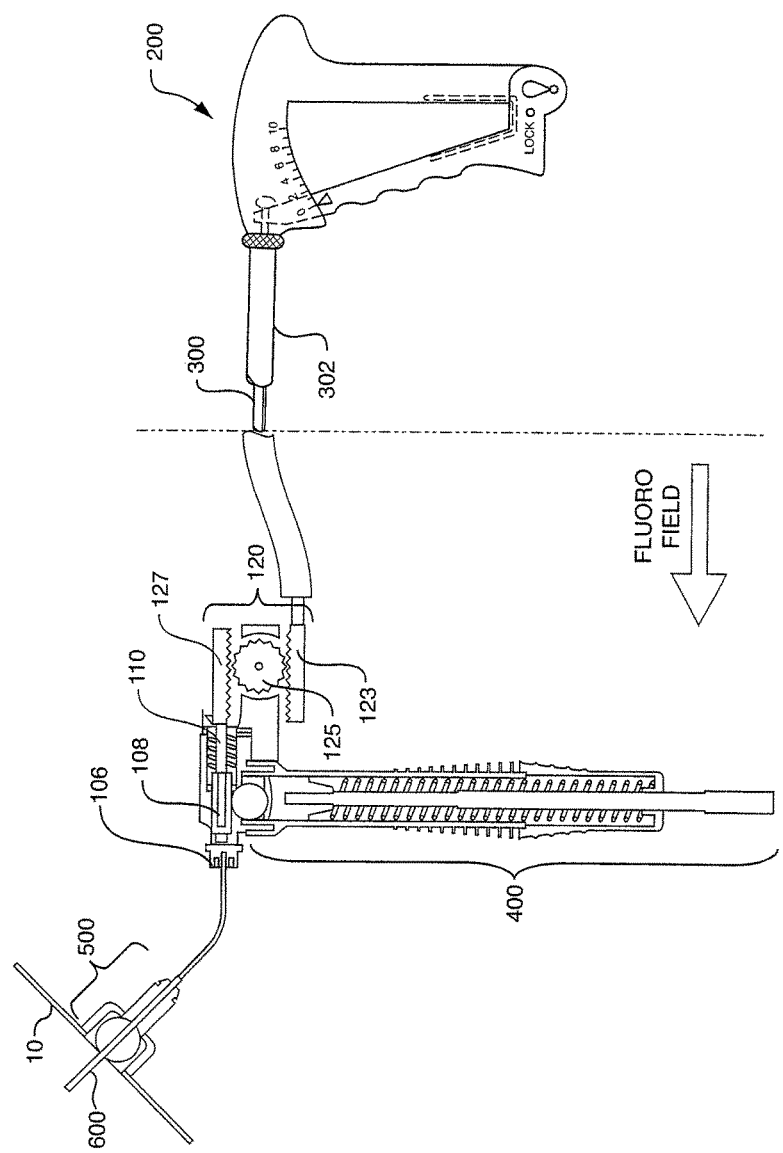
FIG. 3 is a detailed schematic diagram of a remotely-activated injection device according to another embodiment of the invention.

FIG. 3 is a detailed schematic diagram of a remotely-activated injection device according to another embodiment of the invention. In this embodiment, pump 100 defines injection chamber 108 having exit opening 106. Piston 110 is disposed within an inner surface of injection chamber 108 for applying a force against the fluorescent probe material in order to push the material from the injection chamber through exit opening 106.

Piston driver 120 engages piston 110 to allow axial movement of the piston along an axis defined by the end portions of injection chamber 108 toward exit opening 106. The second end of flexible cable 300 engages piston driver 120 allowing actuator 200 to control piston driver 120 by responsive movements of cable 300. In particular, the clinician operates actuator 200 at a safe distance outside the range of the harmful fluoro field.

In the illustrated embodiment, piston driver 120 is a gear mechanism, which includes wheel 125 having a perimeter of teeth. Wheel 125 engages the teeth of two diametrically opposing elements 123, 127. Element 127 has one end mounted to an outer surface of piston 110 that is external to injection chamber 108, while element 123 has one end coupled to the engaging end of cable 300.

When actuator 200 is engaged, causing a responsive movement of the cable away from pump 100, element 123 engages wheel 125 causing a rotational movement. This rotational movement in turn causes wheel 125 to engage element 127, causing piston 110 to move axially along the inner surface of injection chamber 108 toward exit opening 106. As piston 110 moves, a force is exerted against the fluorescent probe material, thereby pushing the material through exit opening 106, where it is transferred to the patient through hollow bone needle 600.

Figure 4:
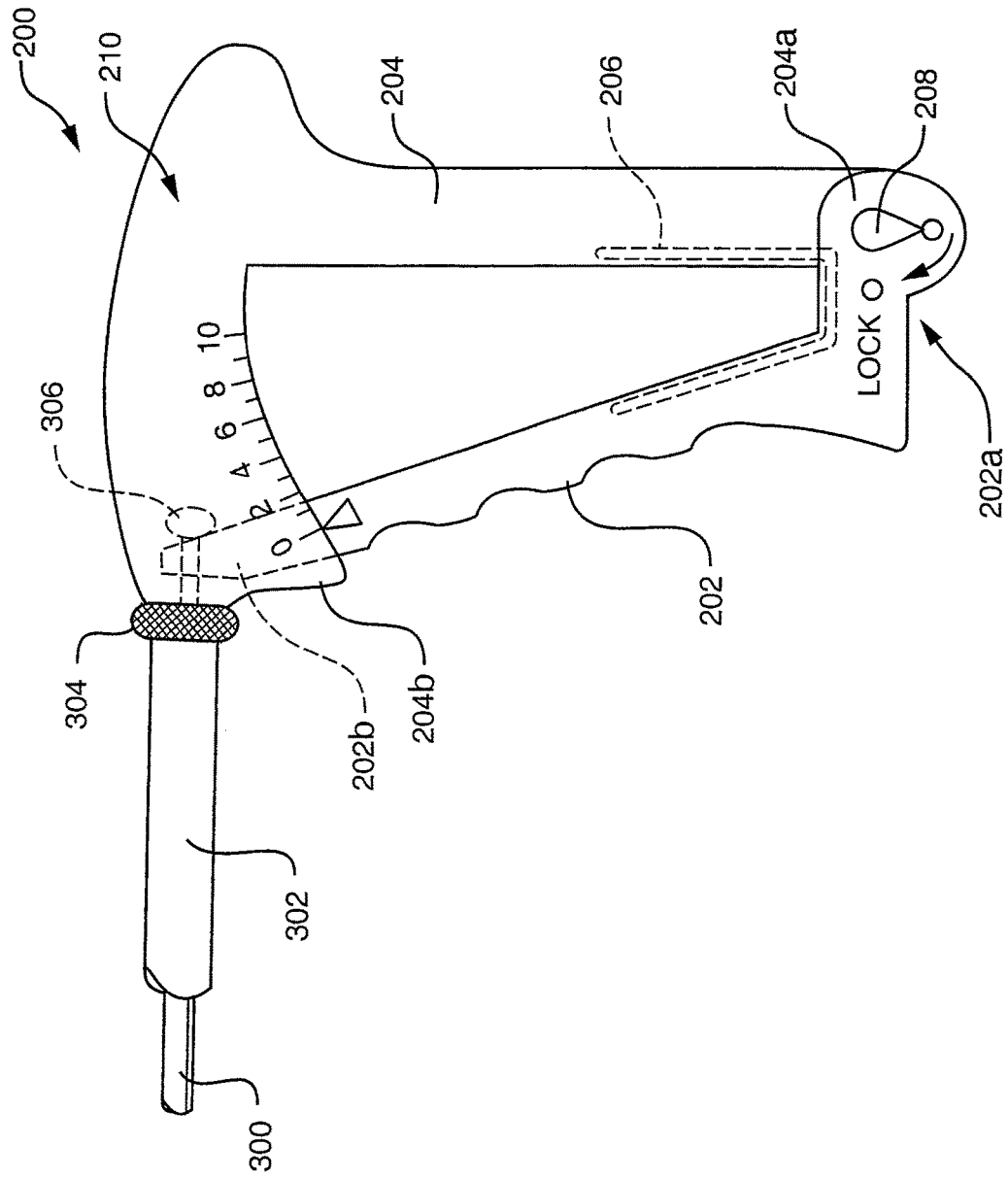
FIG. 4 is a diagram illustrating an arrangement of the actuator and the cable according to the embodiment of the invention of FIG. 3.

FIG. 4 is a diagram illustrating an arrangement of the actuator and the cable according to one embodiment. In the illustrated embodiment, actuator 200 includes lever 202 pivotally-coupled to handheld base 204. In particular, lever portion 202a is pivotally-coupled to the base at base portion 204a, allowing lever 202 to move radially from a steady state position toward base 204. Lever portion 202b, in turn, is coupled to one end of cable 300. By gripping lever 202 toward base 204, lever portion 202b moves radially within base 204, thereby causing responsive movement of cable 300. The responsive movement of cable 300 engages pump 100 causing the injection of the fluorescent material into the patient.

Return spring 206 can be employed to cause lever 202 to return back to its original position as the grip on the lever is released. Actuator 200 can also include locking switch 208 for locking the radial position of lever 202, thereby preventing further responsive movement of cable 300. Base 204 can also include indicator 210 which relates the radial position of lever 202 to the volume of material injected into the patient (e.g., zero to 10 cc). Actuator 200 can be implemented in a variety of ways known to those skilled in the art to enable responsive movements of a cable.

In the illustrated embodiment, cable 300 is a tension cable. Semi-rigid housing 302 is coupled to actuator 200 by connector 304. Cable 300 is fed through housing 302 into actuator 200 where it is coupled to lever portion 202b. According to one embodiment, the cable is fed through a hole in lever portion 202b and held in place by knob 308. Thus, as lever portion 202b radially moves within base 204, cable 300 moves in response. The cable can also be implemented using a variety of cable types known to those skilled in the art for engaging a piston driver.

Figure 5:
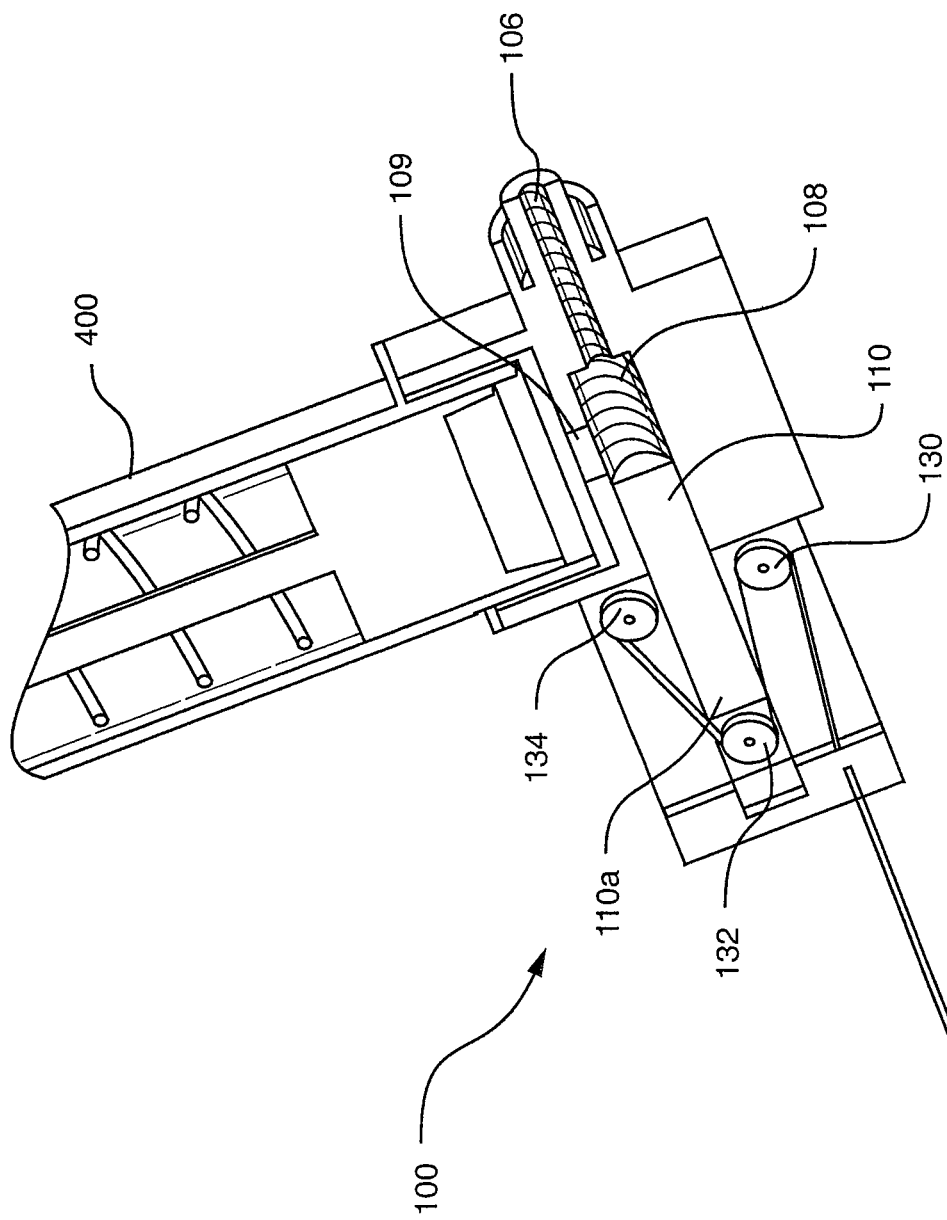
FIG. 5 is a schematic diagram illustrating a piston driver according to another alternative embodiment of the invention.

FIG. 5 is a schematic diagram illustrating a piston driver according to another alternative embodiment of the invention. In this embodiment, the piston driver is a pulley mechanism, including at least three pulley wheels 130, 132, and 134 positioned relative to piston 110. For example, pulley wheels 130 and 134 are mounted on opposing sides of piston 110, and pulley wheel 132 is positioned at the head end of piston 110a that is external to injection chamber 108. Cable 300 is fed through the pulley mechanism, such that a force from the cable can be applied to pulley wheel 132 in the direction of the head end of piston 110a. For example, when actuator 200 causes responsive movement of cable 300 away from pump 100, cable 300 exerts a force against pulley wheel 132 pushing it against the head end of piston 110a. This allows piston 110 to move axially within injection chamber 108 toward exit opening 106, resulting in the injection of the fluorescent probe material.

The fluorescent probe material can be supplied to injection chamber 108 from reservoir 400 through opening 109, as shown. For more information regarding the fluid communication of the reservoir and the injection chamber, refer to U.S. Patent Application Publication US2002/0156483 entitled "Vertebroplasty Injection Device and Bone Cement Therefor," the entire teachings of which are incorporated herein by reference.

Figure 6:
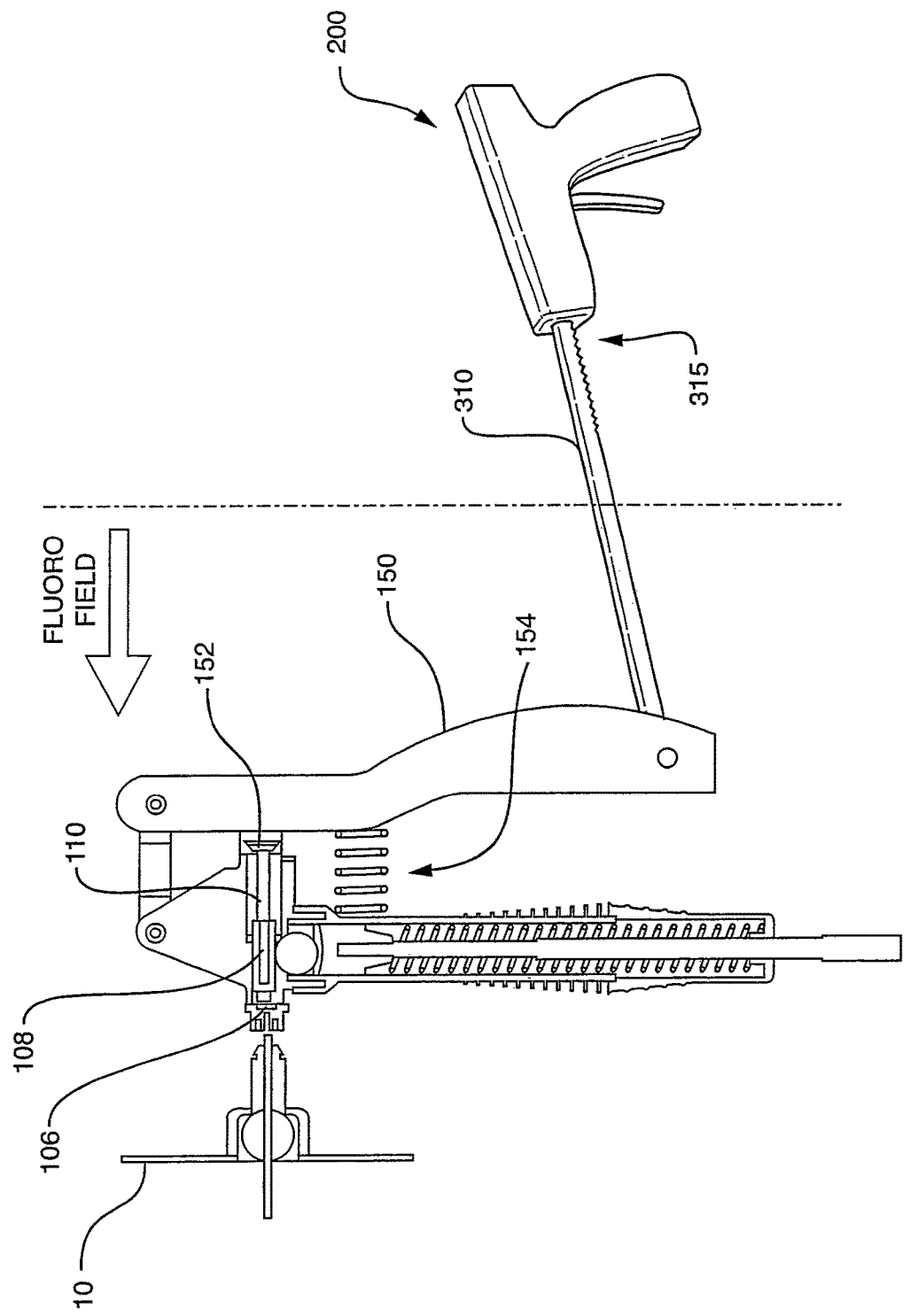
FIG. 6 is a detailed schematic diagram of a remotely-activated vertebroplasty injection device according to still another alternative embodiment of the invention.

FIG. 6 is a detailed schematic diagram of a remotely-activated vertebroplasty injection device according to still another alternative embodiment of the invention. In this embodiment, pump 100 includes lever 150, which provides a mechanical advantage in engaging a plunger. The plunger includes shaft 152 mounted to an outer surface of piston 110 that is external to injection chamber 108. For more information regarding the illustrated pump, refer to U.S. Patent Application Publication US2002/0156483, filed Feb. 15, 2001, the entire teachings of which are incorporated herein by reference.

To remotely activate injection pump 100, the cable coupling injection pump 100 to actuator 200 is rigid rod 310. In particular, one end of rod 310 is attached to the lever, while the other end engages actuator 200. In this embodiment, actuator 200 can be implemented using a ratchet and pawl design, in which the actuator causes rod 310 to move toward lever 150 when the trigger (i.e., ratchet) is applied and engages teeth 315 of rod 310 (i.e., pawl).

As rod 310 pushes against lever 150, a force is exerted against shaft 152, which is attached to piston 110. Thus, the applied force allows piston 110 to move axially in injection chamber 108 toward exit opening 106, through which the flourescent material is injected. Return spring 154 can be employed to return lever 150 back to its original position as rod 310 is retracted back to actuator 300.

As shown in FIGS. 3 and 5, bone needle 600 is inserted through anchor 500, which mounts injection pump 100 to patient 10. The bone need can be straight as shown or bent at a angle (e.g., 90 degrees) in order to remove the pump outside of the fluoro field. Anchor 500 fixes the positioning of the bone needle within the vertebral body, preventing further movement. By anchoring the pump to the patient, the need for an extension tube is avoided, allowing for greater control and reduced pressure concerns.

Figure 7:
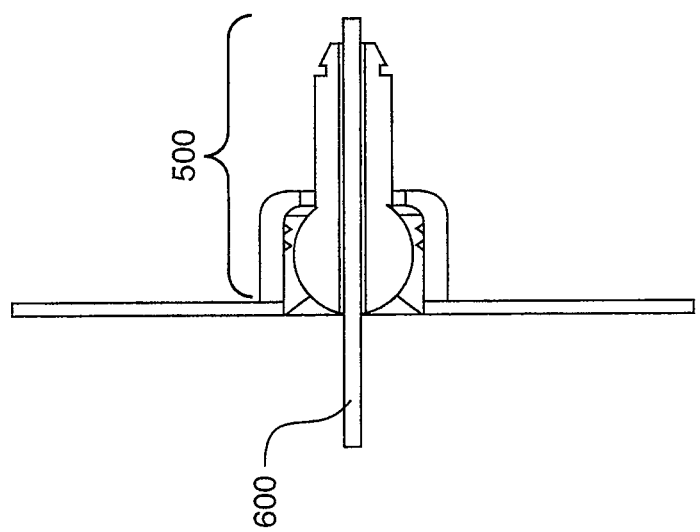
FIG. 7 is a schematic diagram illustrating the anchor according to one embodiment. of the invention.

FIG. 7 is a schematic diagram illustrating the anchor according to one embodiment. In some embodiments, the anchors that are used are disclosed in U.S. patent application Ser. No. 10/259,689, entitled "Novel Device for Advancing a Functional Element, filed on Sep. 30, 2002, the entire teachings of which are incorporated by reference.

Figure 8:
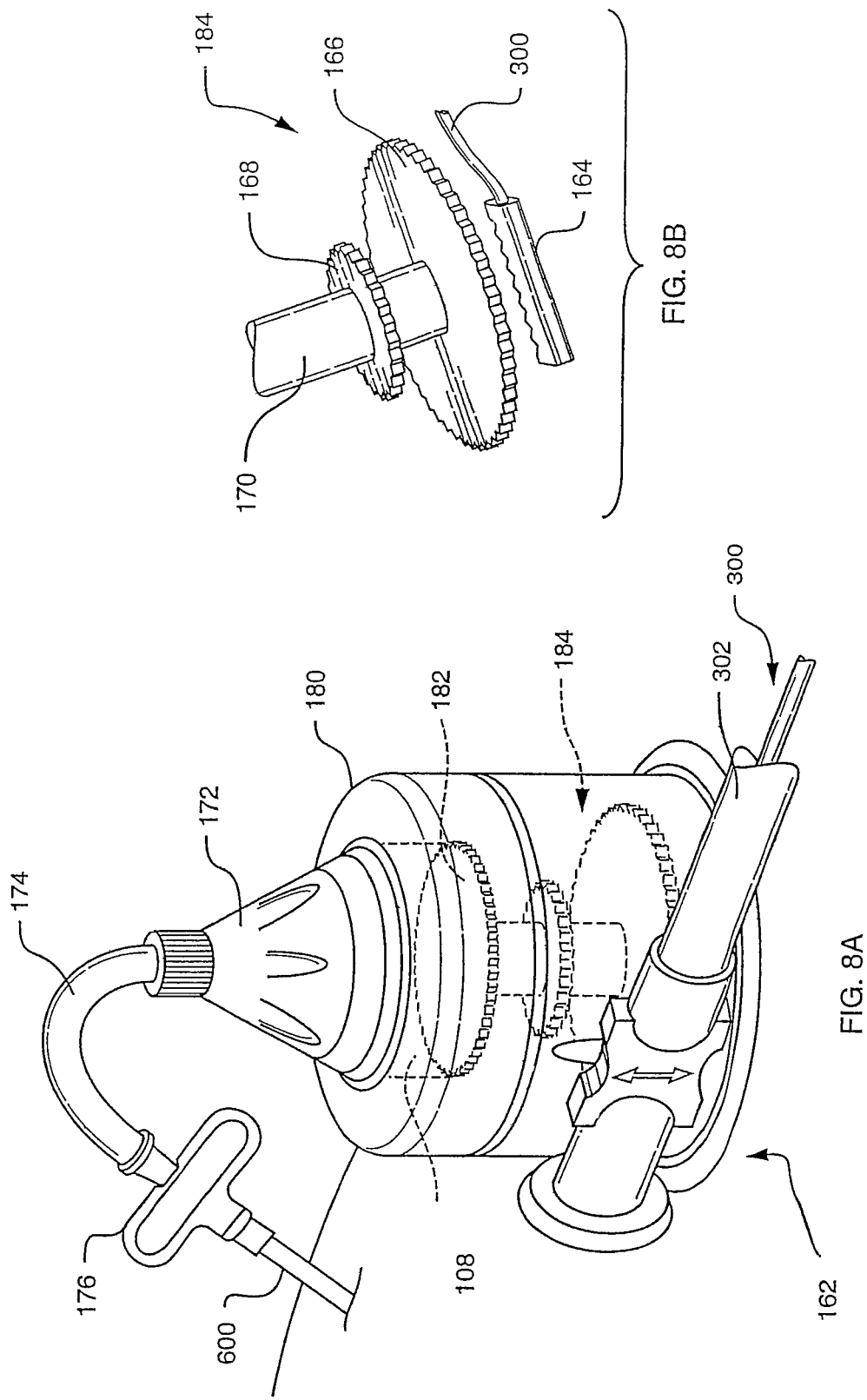
FIG. 8A is a diagram illustrating a remotely-activated vertebroplasty injection device according to a further alternative embodiment.
FIG. 8B is a diagram illustrating the piston driver of FIG. 8A in more detail according to one embodiment.

FIG. 8A is a diagram illustrating a remotely-activated vertebroplasty injection device according to a further alternative embodiment. In this embodiment, the pump includes a housing 180 which is attached to the patient using an adhesive pad 162. The housing 180 includes a funnel-shaped exit 170, which is coupled to flexible tubing 174. The flexible tubing 174 is further coupled to a bone needle 600 by a needle coupler 176. The housing 180 includes a injection chamber, referred to as cement chamber 108, in which a piston 182 moves axially within the chamber. In the illustrated embodiment, the piston 182 moves vertically toward the funnel-shaped exit 172.

The piston 182 is engaged by a piston driver 184 (shown in more detail in FIG. 8B) to allow axial movement of the piston. A cable 300 is fed into the housing 180 through a cable housing 302. The engaging end of the cable 300 engages the piston driver 184 to control the movement of the piston 182.

In particular, the actuator (not shown) controls the piston driver 184 by responsive movement of the cable 300 to cause axial movement of the piston toward the funnel-shaped exit 172 of the chamber 108. As the piston moves vertically, the flourescent probe cement is forced up into the funnel-shaped exit 172, through flexible tubing 174, and into the needle coupler 176 for injection into the vertebral body of the patient through the bone needle 600.

FIG. 8B is a diagram illustrating the piston driver of FIG. 8A in more detail according to one embodiment. The piston driver 184 includes a screw shaft 170 having one end mounted to a surface of the piston 182, external to the cement chamber 108. The opposite end of the shaft 170 is positioned through the open centers of gear wheels 166 and 168, each having a perimeter of teeth. The engaging end of cable 300 is attached to an element 164 having teeth which can engage either one of the gear wheels 166, 168. When the actuator (not shown) causes a responsive movement away from the pump, the responsive movement causes a rotational movement of the gear wheel 166, 168, which further causes the screw shaft 170 to move in an upward direction toward the cement chamber 108. As the shaft 170 moves, the piston 182 moves in conjunction toward the funnel-shaped exit 172, forcing the material out of the chamber 108. According to one embodiment, the gear wheels 166 and 168 can have different diameters. Thus, the flourescent probe material (e.g., flourescent bone cement) can be injected at different rates.

In some embodiments, the vertebral body is first prepared by lavage to create a porous matrix suitable for accepting the cement under low pressure. In some embodiments, the lavage procedures that are used are disclosed in U.S. patent application Ser. No. 10/301,451, entitled "Methods of Performing Embolism-Free Vertebroplasty and Devices Therefor," filed Nov. 21, 2002, the entire teachings of which are incorporated by reference herein.

There is a need to improve the safety of the vertebroplasty, and in particular to reduce the frequency and severity of pulmonary embolism in vertebroplasty procedures.

Figure 9:
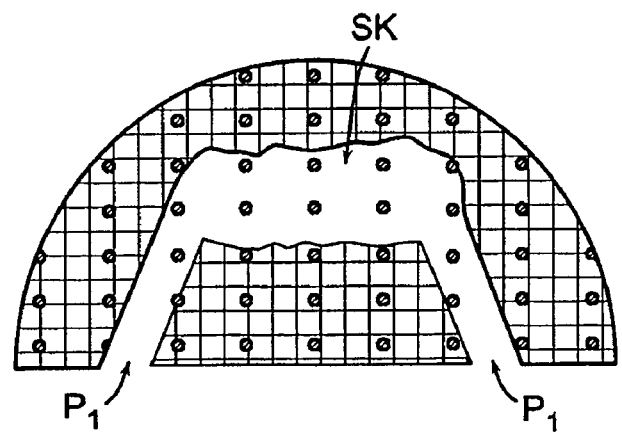
FIG. 9 discloses a cross-section of a vertebral body prepared according to an embodiment of the present invention, wherein a second passageway in connection with the skeleton is provided.

The present inventors believe that high pressures associated with conventional vertebroplasty procedures may be due in part to the essentially closed nature of the vertebral body. That is, even when cement is injected into a volume having significant open porosity, the cement nonetheless reduces the porosity of the volume, so that the last increments of cement that fill that volume may need to be injected under high pressure. Accordingly, the present inventor believes that a pressure relief means may also be used as a way of relieving pressure built up by a cement injection. One particular pressure relief means comprises a second passageway extending from the outside of the vertebral body to the skeleton. FIG. 9 discloses a cross section of a vertebral body having a first passageway P, a skeleton portion SK, and a second passageway P2. This second passageway provides the cement with a low pressure route for relieving the excess pressure produced by the filling that could exacerbate embolisms.

In some embodiments, a bone cement pressure relief device is disposed within the bone cement pressure relief passage to minimize contact between the pressurized cement and the soft tissue of the vertebral body. Preferred embodiments of this device include those of the bone cement delivery device.

In some embodiments; the cements are osteobiologic. In some embodiments, the osteobiologic compositions that are used are disclosed in U.S. Provisional Patent Application Ser. No. 60/448,221, entitled "Omnibus In-Situ Formed Intervertebral Fusion Device," filed Feb. 14, 2003, the entire teachings of which are incorporated by reference herein.

EQUIVALENTS

While this invention has been particularly shown and described with references to preferred embodiments thereof, it will be understood by those skilled in the art that various changes in form and details can be made therein without departing from the scope of the invention encompassed by the appended claims.

What is claimed is:

1. A handheld pumping system comprising:
   an actuator;
   a hydraulic piston driver;
   a housing operatively connecting the actuator to the hydraulic piston driver;
   a pump defining an injection chamber having an exit opening connectable to a bone needle, the injection chamber containing bone cement and including a piston operatively connected to the hydraulic piston driver so that actuation of the actuator results in the receiving of pressurized fluid by the hydraulic piston driver to selectively actuate the hydraulic piston driver to drive the piston to force said bone cement from the injection chamber through the exit opening;
   a cement pressure relief device on the handheld pumping system for minimizing contact between pressurized cement and other tissue.

2. The system of claim 1, further comprising a handheld base supporting the actuator for the hydraulic driver.

3. The system of claim 2, further comprising a lever portion pivotally coupled to the handheld base for selectively actuating the hydraulic driver.

4. The system of claim 3, wherein the housing is semi-rigid and connects to the handheld base and the hydraulic driver is actuated through the semi-rigid housing.

5. A handheld pumping system comprising:
   a hydraulic fluid for pressurization;
   a chamber containing the hydraulic fluid;
   an actuator for applying pressure to the hydraulic fluid;
   a housing connecting the actuator to the chamber containing the hydraulic fluid;
   a container of bone cement connected to said housing and receiving pressurized fluid to selectively force said bone cement from said container;
   a pump defining an injection chamber having an exit opening connectable to a bone needle, the injection chamber containing bone cement and including a piston operatively connected to a hydraulic piston driver so that actuation of the actuator results in the receiving of pressurized fluid by the hydraulic piston driver to selectively actuate the hydraulic piston driver to drive the piston to force said bone cement from the injection chamber through the exit opening;
   a cement pressure relief device on the handheld pumping system for minimizing contact between pressurized cement and other tissue.

6. The system of claim 5, further comprising a handheld base supporting the actuator for the hydraulic driver.

7. The system of claim 6, further comprising a lever portion pivotally coupled to the handheld base for selectively actuating the hydraulic driver.

8. The system of claim 7, wherein the housing is semi-rigid and connects to the handheld base and the hydraulic driver is actuated through the semi-rigid housing.

* * * * *